(12) United States Patent
Huang et al.

(10) Patent No.: US 9,952,209 B2
(45) Date of Patent: Apr. 24, 2018

(54) IRON OXIDE-GOLD CORE-SHELL NANOPARTICLES AND USES THEREOF

(71) Applicant: University of Memphis Research Foundation, Memphis, TN (US)

(72) Inventors: Xiaohua Huang, Cordova, TN (US); Saheel Bhana, Memphis, TN (US)

(73) Assignee: The University of Memphis Research Foundation, Memphis, TN (US)

( * ) Notice: Subject to any disclaimer, the term of this patent is extended or adjusted under 35 U.S.C. 154(b) by 583 days.

(21) Appl. No.: 14/321,770

(22) Filed: Jul. 1, 2014

(65) Prior Publication Data

US 2015/0037818 A1 Feb. 5, 2015

Related U.S. Application Data

(60) Provisional application No. 61/841,927, filed on Jul. 1, 2013.

(51) Int. Cl.

| | | |
|---|---|---|
| G01N 33/543 | (2006.01) | |
| G01N 33/58 | (2006.01) | |
| C23C 18/44 | (2006.01) | |
| C23C 18/16 | (2006.01) | |
| C23C 18/30 | (2006.01) | |
| C23C 18/18 | (2006.01) | |
| H01F 1/00 | (2006.01) | |
| B22F 1/00 | (2006.01) | |
| B22F 1/02 | (2006.01) | |
| B22F 9/24 | (2006.01) | |

(52) U.S. Cl.
CPC ..... *G01N 33/54346* (2013.01); *B22F 1/0018* (2013.01); *B22F 1/025* (2013.01); *C23C 18/1635* (2013.01); *C23C 18/1637* (2013.01); *C23C 18/1651* (2013.01); *C23C 18/1889* (2013.01); *C23C 18/30* (2013.01); *C23C 18/44* (2013.01); *G01N 33/587* (2013.01); *H01F 1/0054* (2013.01); *B22F 9/24* (2013.01); *B22F 2001/0037* (2013.01); *C23C 18/168* (2013.01); *G01N 2446/20* (2013.01)

(58) Field of Classification Search
CPC ..... C23C 18/1635; C23C 18/30; C23C 18/44; C23C 18/1637; C23C 18/1889; C23C 18/1651; C23C 18/168; G01N 33/587; G01N 33/54346; G01N 2446/20; H01F 1/0054; B22F 1/0018; B22F 1/025; B22F 2001/0037; B22F 9/24
See application file for complete search history.

(56) References Cited

U.S. PATENT DOCUMENTS

2013/0123145 A1* 5/2013 Chakravarthy .. G01N 33/54346
506/16

OTHER PUBLICATIONS

Liang et al., Iron oxide/gold core/shell nanoparticles for ultrasensitive detection of carbohydrate-protein interactions. Anan. Chem. 2009, vol. 81, pp. 7750-7756.*

Zhang et al., GoldMag nanoparticles with core/shell structure: characterization and application in MR imaging. J. Nanopart Res. 2011, vol. 13, pp. 3867-3876.*

(Continued)

*Primary Examiner* — Shafiqul Haq
(74) *Attorney, Agent, or Firm* — Mintz Levin Cohn Ferris Glovsky and Popeo, P.C.; Peter F. Corless; Carolina E. Säve

(57) ABSTRACT

Magnetic-optical iron oxide-gold core-shell nanoparticles are disclosed. Methods for making and using the nanoparticles are also disclosed.

15 Claims, 17 Drawing Sheets

Step 1: Preparation of silver-adsorbed iron oxide nanoparticles

Step 2: Growth of gold shell onto silver-adsorbed iron oxide nanoparticles

Schematic illustration of the preparation of iron oxide-gold core-shell nanoparticles.

(56) References Cited

OTHER PUBLICATIONS

Cai et al., Applicaitons of gold nanoparticles in cancer nanotechnology. Nanotechnol Sci Appl. 2008, pp. 1-27.*
Fan et al. Multifunctional plasmonic shell-magnetic core nanoparticles for targeted diagnostics, isolation, adn photothermal destruction of tumor cells. ACS Nano 2012, vol. 6, No. 2, pp. 1065-1073.*
Lu et al. Multifunctional oval-shaped gold-nanoparticle-based slective detection of breast cancer cells using simple calorimetric and highly sensitive two-photon scattering assay. ACS Nano 2010, vol. 4, No. 3, pp. 1739-1749.*
Sajanlal et al. Anisotropic nanomaterials: structure, growth, assembly, and functions. Nano Reviews 2011, vol. 2, No. 5883, pp. 1-62.*

\* cited by examiner

*Step 1: Preparation of silver-adsorbed iron oxide nanoparticles*

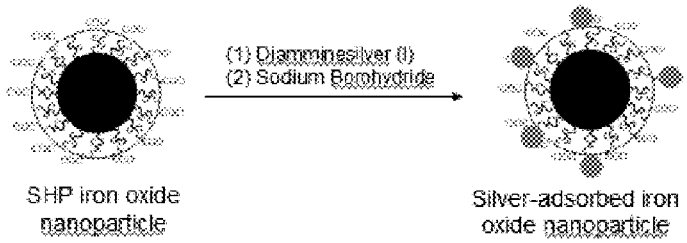

*Step 2: Growth of gold shell onto silver-adsorbed iron oxide nanoparticles*

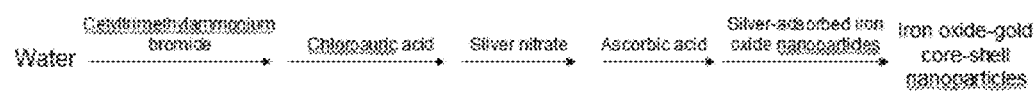

Figure 1: Schematic illustration of the preparation of iron oxide-gold core-shell nanoparticles.

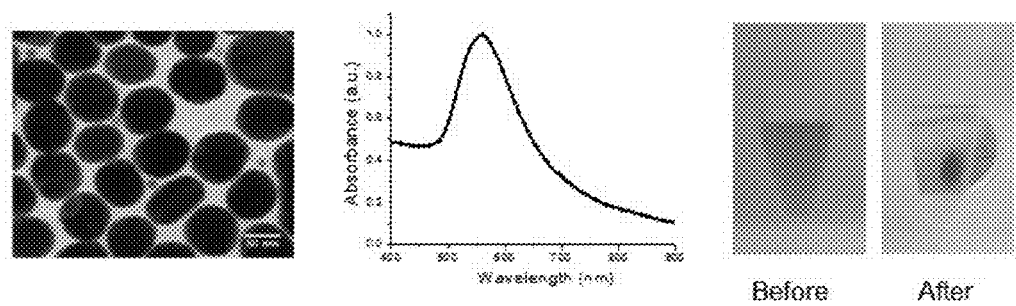

Figure 2: Characterization of iron oxide-gold core-shell nanospheres. Left: Transmission electron microscope image; Middle: Absorption spectrum; and Right: Magnetic separation with an external permanent magnet.

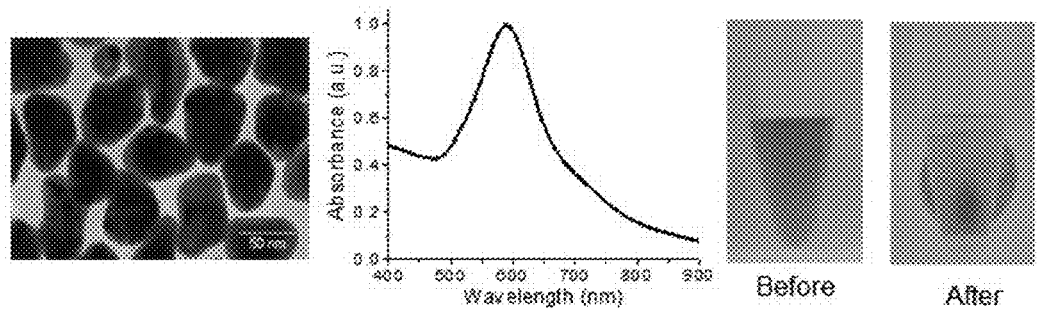

Figure 3: Characterization of iron oxide-gold core-shell nanoovals. Left: Transmission electron microscope image; Middle: Absorption spectrum; and Right: Magnetic separation with an external permanent magnet.

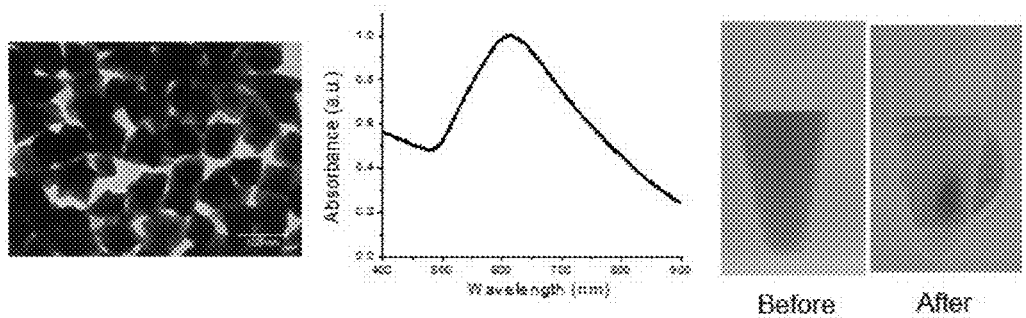

Figure 4: Characterization of iron oxide-gold core-shell nanoflowers. Left: Transmission electron microscope image; Middle: Absorption spectrum; and Right: Magnetic separation with an external permanent magnet.

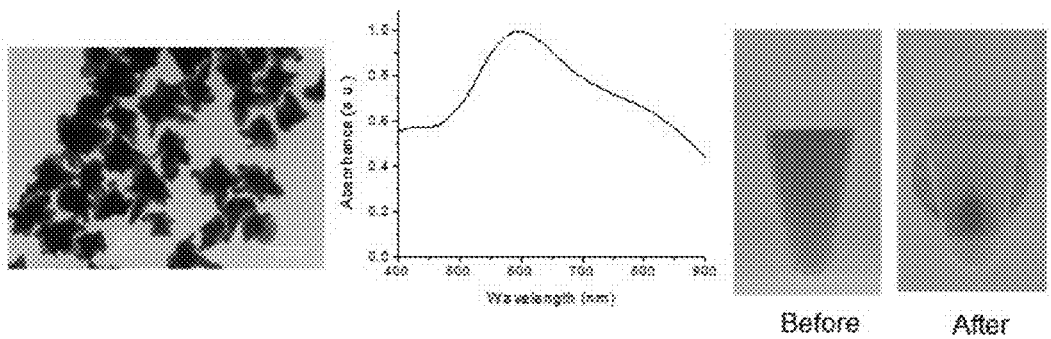

Figure 5: Characterization of iron oxide-gold core-shell nanostars. Left: Transmission electron microscope image; Middle: Absorption spectrum; and Right: Magnetic separation with an external permanent magnet.

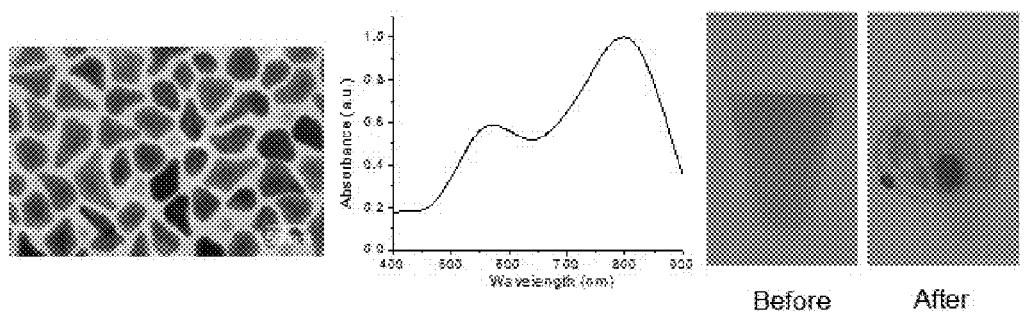

Figure 6: Characterization of iron oxide-gold core-shell nanopins. Left: Transmission electron microscope image; Middle: Absorption spectrum; and Right: Magnetic separation with an external permanent magnet.

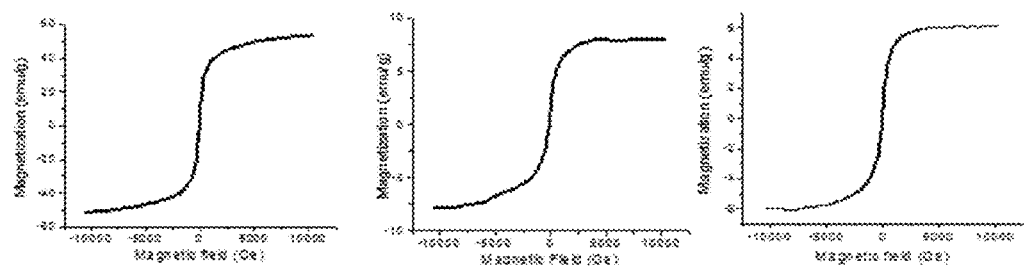

Figure 7: Magnetization curves at room temperature. Left: SHP 25 iron oxide nanoparticles; Middle: Iron oxide-gold core-shell nanoovals; and Right: Iron oxide-gold core-shell nanopins.

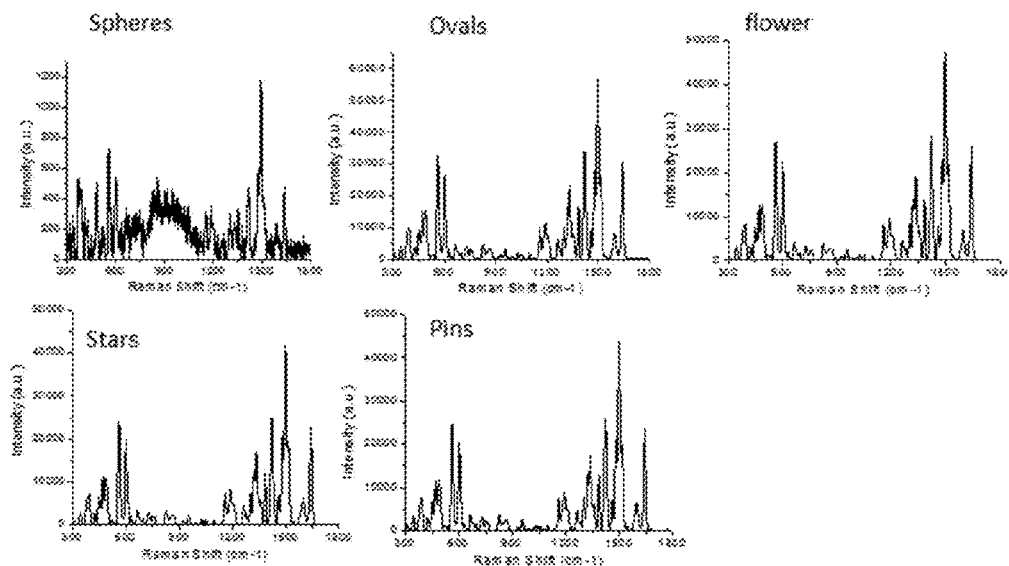
Figure 8.
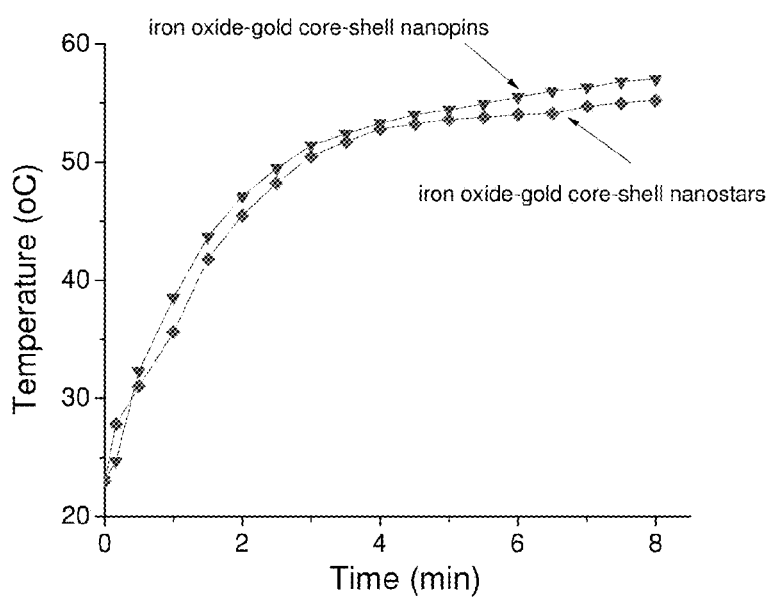
Figure 9: Photothermal effects of iron oxide-gold core-shell nanostars and nanopins. Concentration of the nanoparticles: 0.01 nanomolar; Laser wavelength: 785 nanometer; Laser intensity: 0.55 W/cm$^2$.

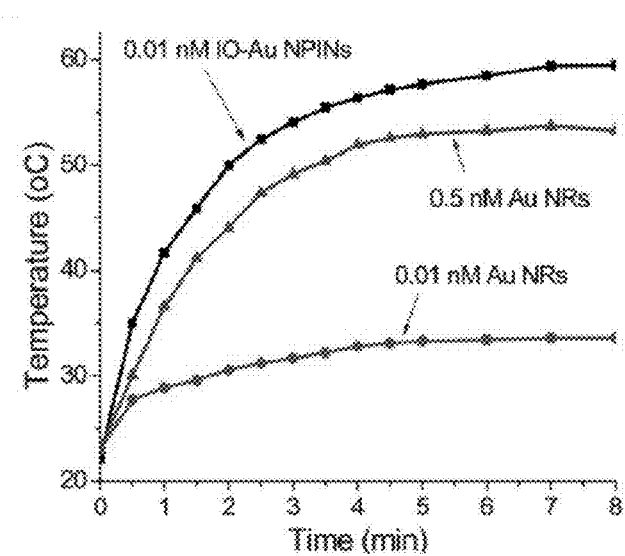
Figure 10: Comparison of the photothermal effects of iron oxide-gold core-shell nanopins with gold nanorods. Laser wavelength: 785 nanometer; Laser intensity: 0.55 W/cm$^2$.

Figure 14. Detection of prelabeled SK-BR-3 cells spiked into whole blood. SK-BR-3 cells were labeled with anti-EpCAM/IO-Au SERS NOVs and anti-HER2/IO-Au SERS NOVs, then purified and dispersed in human whole blood for on-line magnetic capture and SERS detection.

Figure 16. Detection of SK-BR-3 cells spiked into whole blood. Human whole blood containing specified number of SK-BR-3 cells was incubated with anti-EpCAM/IO-Au SERS NOVs for 30 min at room temperature, followed by on-line magnetic capture and SERS detection.

(A) SERS spectra of 10 pM QSY21-adsorbed IO-Au NHGs, (B) SERS signals of 10 pM QSY21-adsorbed IO-Au NSs and (C) Raman spectrum of 10 mM free QSY21 solution Excitation wavelength: 785 nm; power: 25 mW; acquisition time: 1 s and 10 x objective.

IRON OXIDE-GOLD CORE-SHELL NANOPARTICLES AND USES THEREOF

CROSS-REFERENCE TO RELATED APPLICATIONS

This application claims the benefit of and priority to U.S. Provisional Patent Application No. 61/841,927, filed Jul. 1, 2013, the contents of which are incorporated herein by reference.

BACKGROUND OF THE INVENTION

Hybrid nanomaterials possessing dual magnetic/optical properties are of considerable interests to many areas, ranging from material science to biology and medicine. They are promising for a broad range of applications including catalysis, energy conversion, biological separation, medical diagnosis and treatment, superior to magnetic and plasmonic nanostructures alone. Iron oxide (magnetite or maghemite)-gold (IO-Au) core-shell nanoparticles (NPs) are magnetic-optical hybrid nanomaterials that have been studied due to their highly integrated structure, facile surface chemistry modification and biocompatibility. A variety of methods has been reported to make iron oxide-gold core-shell nanoparticles (see, e.g., L. Wang, H. Y. Park, S. I. Lim, M. J. Schadt, D. Mott, J. Luo, X. Wang, C. J. Zhong. J. Mater. Chem., 2008, 18, 2629-2635). However, preparation of high quality IO-Au core-shell NPs is challenging.

During the last decade, considerable efforts have been focused on the preparation of IO-Au core-shell NPs [1-15]. These methods can be divided into three major categories: (1) reduction of gold salt ($Au^{3+}$) in the presence of IO NPs, (2) reduction of gold salt ($Au^{3+}$) in the presence of Au-seeded IO NPs and (3) reduction of gold salt ($Au^{3+}$) in the presence of IO or Au-seeded IO NPs with an organic gap. Direct reduction of Au ions in the presence of IO NPs can lead to jagged Au surfaces on IO NPs. In 2010, Jin et al introduced a polymer gap between Au and IO and used chemical reduction of $Au^{3+}$ ions in the presence of polymer-coated IO NPs [11]. Although this approach overcomes the problem of the lattice mismatching of the two components, direct reduction of $Au^{3+}$ to $Au^0$ with strong reducing agents usually leads to uncontrolled nucleation of discrete Au NPs in solution or attached on the surface of IO NPs. Formation of stable and monodisperse Au seed-IO NPs by electrostatic interaction between Au and IO NPs without causing aggregation is difficult because of the opposite charge of Au seed and IO NPs. Importantly, these methods are limited to the preparation of IO-Au NPs in spherical shapes.

These IO-Au nanospheres generally have localized surface plasmon resonance (LSPR) absorption in the visible spectra region, unless they are large (>100 nm) [13] or they have an ultrathin Au shell with a polymer gap [11].

A major limitation to existing methods is the lack of the ability to make anisotropic iron oxide-gold core-shell nanoparticles (NPs). Compared to isotropic spherical nanoparticles, anisotropic nanoparticles offer better and/or new properties due to their high curvature and polarization-sensitive structure. Anisotropic nanoparticles can tune the optical properties of the hybrid nanoparticles in a widespread spectral region, which is highly desirable for many material and biomedical applications. The preparation of iron oxide (IO)-Au core-shell nanoparticles in star shapes has been reported [18, 19]. However, the reported method for making these nanoparticles included harsh synthetic conditions (such as high temperature and toxic organic solvent) and lack of the ability to tune the shape of the hybrid nanoparticles. In addition, the final products are limited to only IO-Au nanostars with large size (>100 nm).

It would be advantageous to have a facile and versatile method that can provide iron oxide-gold nanoparticles in a variety of shapes with only slight modification of the experimental conditions.

SUMMARY OF THE INVENTION

In one aspect, the invention provides iron oxide-gold core-shell nanoparticles (IO-Au NPs) which can have a variety of shapes.

In one aspect, the invention provides a magnetic-optical iron oxide-gold core-shell nanoparticle comprising a silver-adsorbed iron oxide nanoparticle core. In certain embodiments, the IO-Au NP is a nanosphere. In certain embodiments, the IO-Au NP is anisotropic (non-spherical), e.g., has a major axis and a minor axis which differ by at least about 10%. In certain embodiments, the anisotropic IO-Au NP is a nanopin. In certain embodiments, the anisotropic IO-Au NP is a nanostar. In certain embodiments, the anisotropic IO-Au NP is a nanooval. In certain embodiments, the anisotropic IO-Au NP is a nanoflower. In certain embodiments, the anisotropic IO-Au NP is a nanohexagon. In certain embodiments, the nanoparticle is superparamagnetic. In certain embodiments, the magnetic-optical iron oxide-gold core-shell nanoparticle has an average diameter or length along the longest dimension of about 20-150 nm. In certain embodiments, the magnetic-optical iron oxide-gold core-shell nanoparticle has an average gold shell thickness of about 10-20 nm. In certain embodiments, the anisotropic magnetic-optical iron oxide-gold core-shell nanoparticle exhibits surface plasmon absorption between about 550 nm-900 nm.

In another aspect, the invention provides a magnetic-optical iron oxide-gold core-shell nanoparticle comprising an iron oxide nanoparticle core greater than 10 nm in diameter. In certain embodiments, the nanoparticle is anisotropic.

In another aspect, the invention provides a method for producing a IO-Au NP or IO-Au NPs (including anisotropic IO-Au NPs), the method comprising: (a) preparation of silver-adsorbed iron oxide nanoparticles and (b) growth of gold shell onto the silver-adsorbed iron oxide nanoparticles to form iron oxide-gold core-shell nanoparticles. In certain embodiments, step (a) comprises adsorbing silver ions onto superparamagnetic iron oxide nanoparticles, and reduction with a reducing agent to form silver-adsorbed iron oxide nanoparticles. In certain embodiments, diamminesilver ($Ag(NH_3)_2)^+$) ions are the source of silver(I) ions in step (a). In certain embodiments, step (a) comprises adsorbing diamminesilver ions onto superparamagnetic iron oxide nanoparticles, and reduction with a reducing agent to form silver-adsorbed iron oxide nanoparticles. In certain embodiments, the reducing agent is sodium borohydride. In certain embodiments, step (b) comprises (i) providing a solution of a cationic surfactant such as cetyltrimethylammonium bromide (CTAB) (ii) addition of a source of gold(III) ions such as chloroauric acid ($HAuCl_4$) (gold (III)), and silver nitrate; (iii) reducing gold (III) to gold (I) ions using a reducing agent such as ascorbic acid, and (iv) addition of silver-adsorbed iron oxide nanoparticles to the solution of gold (I) ions, such that an iron oxide-gold core-shell nanoparticle is formed. In certain embodiments, step (b) is performed at a temperature of about 30° C. or less. In certain embodiments, step (b) is performed at a temperature of greater than 30° C.

In another aspect, the invention provides a magnetic-optical iron oxide-gold core-shell nanoparticle produced by a method disclosed herein.

In another aspect, the invention provides a method of detecting an analyte or a cell in a sample, the method comprising:

contacting the sample with an iron oxide-gold core-shell nanoparticle capable of specific binding with the analyte or cell (e.g., an iron oxide-gold core-shell nanoparticle of the invention a described herein, which may be anisotropic) and detecting the presence of the iron oxide-gold core-shell nanoparticle, thereby detecting the analyte or cell.

In certain embodiments, the anisotropic iron oxide-gold core-shell nanoparticle is a nanooval. In certain embodiments, the analyte or cell is a cancer cell, such as a circulating tumor cell. In certain embodiments, the sample is whole blood. In certain embodiments, the iron oxide-gold core-shell nanoparticle is conjugated to an antibody capable of specifically binding the analyte. In certain embodiments, the anisotropic iron oxide-gold core-shell nanoparticles are conjugated to an antibody capable of specifically binding the analyte or cell. In certain embodiments, the method includes the step of magnetically separating the anisotropic iron oxide-gold core-shell nanoparticles bond to the analyte or cell from the sample. In certain embodiments, the step of detecting comprises detecting the presence of the anisotropic iron oxide-gold core-shell nanoparticle in an integrated flow system, thereby capturing and detecting the analyte.

BRIEF DESCRIPTION OF THE DRAWINGS

FIG. 1: Schematic illustration of the preparation of iron oxide-gold core-shell nanoparticles.

FIG. 2: Characterization of iron oxide-gold core-shell nanospheres. Left: Transmission electron microscope image; Middle: Absorption spectrum; and Right: Magnetic separation with an external permanent magnet.

FIG. 3: Characterization of iron oxide-gold core-shell nanoovals. Left: Transmission electron microscope image; Middle: Absorption spectrum; and Right: Magnetic separation with an external permanent magnet.

FIG. 4: Characterization of iron oxide-gold core-shell nanoflowers. Left: Transmission electron microscope image; Middle: Absorption spectrum; and Right: Magnetic separation with an external permanent magnet.

FIG. 5: Characterization of iron oxide-gold core-shell nanostars. Left: Transmission electron microscope image; Middle: Absorption spectrum; and Right: Magnetic separation with an external permanent magnet.

FIG. 6: Characterization of iron oxide-gold core-shell nanopins. Left: Transmission electron microscope image; Middle: Absorption spectrum; and Right: Magnetic separation with an external permanent magnet.

FIG. 7: Magnetization curves at room temperature. Left: SHP 25 iron oxide nanoparticles; Middle: Iron oxide-gold core-shell nanoovals; and Right: Iron oxide-gold core-shell nanopins.

FIG. 8: Surface enhanced Raman scattering activities of iron oxide-gold core-shell nanoparticles in different shapes. Surface enhanced Raman signals are from QSY 21 adsorbed onto the nanoparticles. Concentration of the nanoparticles: 0.01 nM; Raman excitation laser: 785 nanometer; Laser power: 25 miniwatts; Acquisition time: 1 second.

FIG. 9: Photothermal effects of iron oxide-gold core-shell nanostars and nanopins. Concentration of the nanoparticles: 0.01 nanomolar; Laser wavelength: 785 nanometer; Laser intensity: 0.55 W/cm$^2$.

FIG. 10: Comparison of the photothermal effects of iron oxide-gold core-shell nanopins with gold nanorods. Laser wavelength: 785 nanometer; Laser intensity: 0.55 W/cm$^2$.

DETAILED DESCRIPTION OF THE INVENTION

Figure 11:
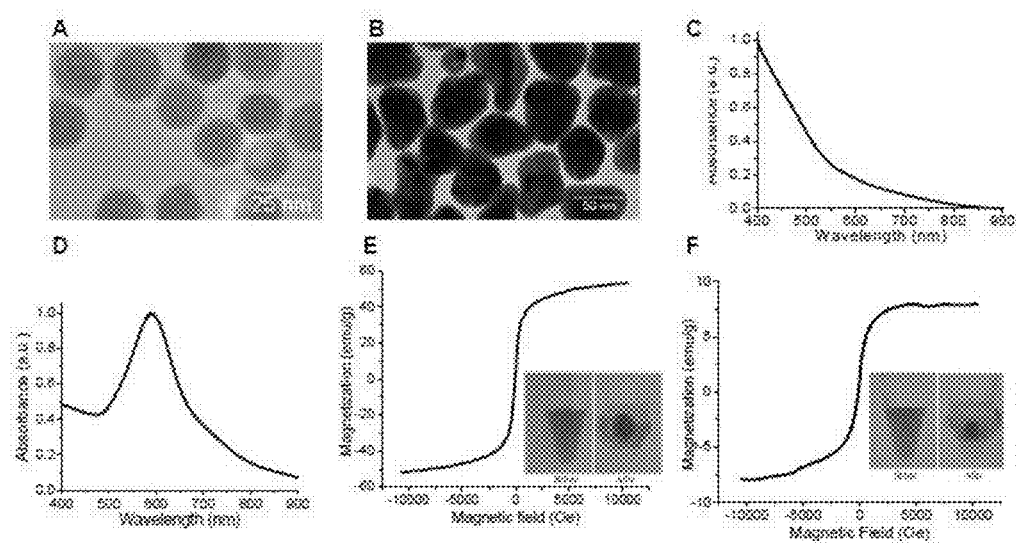
FIG. 11: Structures and properties of iron oxide-gold core-shell nanoparticles (A, C & E) and IO-Au NOVs (B, D & F). (A) & (B) TEM micrographs; (C) & (D) Absorption spectra; (E) & (F) Magnetization curves at room temperature and magnetic separation with permanent magnets. Tehe IO-Au NOVs average 60 nm along the long axis and 50 nm along the short axis with an IO core of about 25 nm in diameter. They are superparamagnetic and have SPR absorption around 590 nm.

In general, the present invention relates to magnetic-optical iron oxide-gold core-shell nanoparticles in different shapes and to methods of making and using them. It has unexpectedly been found that the magnetic-optical iron oxide-gold core-shell nanoparticles of the invention have novel properties making them useful for a variety of applications.

Magnetic-Optical Iron Oxide-Gold Core-Shell Nanoparticles

In one aspect, the invention provides iron oxide-gold core-shell nanoparticles, including, in certain embodiments, anisotropic iron oxide-gold core-shell nanoparticles.

Anisotropic NPs offer much stronger optical properties than spherical ones due to their high curvature structure. For example, the E-field enhancement of Au tripod nanocrystals are 20 times higher than the spherical ones [16]. This would lead to 400 times higher surface enhanced Raman scattering (SERS) activities for Au nanotripod than the spherical Au NPs. Anisotropic NPs could also offer new functions that isotropic spheres do not have based on the polarization sensitive feature for the anisotropic ones. In addition, anisotropic IO NPs can tune the optical properties from visible to near infrared (NIR) region without changing particle size. The NIR window is important for biomedical applications as light in this region is tissue penetrative [17].

Thus, it is very important to develop a facile and versatile method that can lead to the formation of uniform IO-Au NPs in a number of shapes. The present invention provide such a method to prepare uniform IO-Au NPs in several shapes including sphere, oval, flower, star and pin.

As used herein, the terms "nanoparticle" and "nanoparticles" are used interchangeably; thus, for example, a method of making a nanoparticle includes methods of making nanoparticles, and reference to "nanoparticles" also include "a nanoparticle", unless otherwise clear from context.

In certain embodiments, the iron oxide-gold core-shell nanoparticles are nanospheres, nanoovals, nanoflowers, nanopins, nanohexagons or nanostars.

As used herein, the term "nanosphere" refers to a core shell nanoparticle having a substantially spherical shape. As used herein, the term "nanooval" refers to a core shell nanoparticle having an oval or ovoid shape. As used herein, the term "nanoflower" refers to a core shell nanoparticle having a "flower" shape, e.g., a floral form. As used herein, the term "nanopin" refers to a core shell nanoparticle having a pin shape, i.e., an elongated shape having a substantially rounded cross-sectional shape along a principal axis, or having a pointed or conical protrusion or point. As used herein, the term "nanostar" refers to a core shell nanoparticle having a regular or irregular star shape, i.e., a central body having four or more radial projections or protrusions from the central body; a nanostar may be irregular and the projections may have differing lengths, thicknesses and shapes. As used herein, the term "nanohexagon" refers to a core shell nanoparticle having a substantially hexagonal shape in cross-section, e.g., has six substantially equal sides in cross-section.

In certain embodiments, the iron oxide-gold core-shell nanoparticles are anisotropic iron oxide-gold core-shell nanoparticles.

In certain embodiments, the iron oxide-gold core-shell nanoparticles have an average diameter (or length along the longest dimension in the case of anisotropic nanoparticles) of about 20-150 nm, or 30-100 nm, or about 35-60 nm. For example, a nanooval can have dimensions of an average of 60 nm from the tip to base and 50 nm along the base In certain embodiments, the iron oxide-gold core-shell nanoparticles have an average diameter (or length along the longest dimension) of about 1-40 nm.

In certain embodiments, the iron oxide-gold core-shell nanoparticles have an average gold shell thickness of about 10-20 nm, or about 12-18 nm. In certain embodiments, the iron oxide-gold core-shell nanoparticles are anisotropic iron oxide-gold core-shell nanoparticles.

In certain embodiments, the iron oxide-gold core-shell nanoparticles exhibit surface plasmon absorption between about 550 nm-900 nm, or between about 550 nm-610 nm, or about 590 nm. In certain embodiments, the iron oxide-gold core-shell nanoparticles are superparamagnetic.

In certain embodiments, the iron oxide-gold core-shell nanoparticle may also comprise additional components. For example, an anisotropic iron oxide-gold core-shell nanoparticle can be surface-modified or derivatized with a material capable of binding to an analyte, antigen, cell or other moiety. For example, an anisotropic iron oxide-gold core-shell nanoparticle can be conjugated to an antibody capable of specific binding to an antigen, including cell-surface antigens. Thus, an anisotropic iron oxide-gold core-shell nanoparticle can be targeted to specifically bind to an analyte or cell type, which permits separation of the analyte and detection of the present or absence of the analyte (see, e.g., Example 2 herein).

The invention also provides methods of making iron oxide-gold core-shell nanoparticles, and iron oxide-gold core-shell nanoparticles made by any of the methods disclosed herein. See also the Examples herein, and Appendix A, which attached to this disclosure and is incorporated herein by reference. In certain embodiments, a method according to the invention includes two steps: (1) Formation of silver-adsorbed superparamagnetic iron oxide nanoparticles (e.g., diamminesilver ions are adsorbed onto polymer-coated iron oxide nanoparticles, followed by reduction with sodium borohydride to form silver-adsorbed iron oxide nanoparticles); and (2) Formation of iron oxide-gold nanoparticles in different shapes (e.g., a growth solution containing chloroauric acid, a cationic surfactant such as cetyl trimethylammonium bromide, and silver nitrate is prepared and kept at room temperature; to the growth solution, a reducing agent such as ascorbic acid is added, followed by addition of silver-adsorbed iron oxide nanoparticles which lead to the formation of iron oxide-gold core-shell nanoparticles; changing the concentrations of diamminesilver ions in the first step, silver nitrate and ascorbic acid in the second step and the duration of the addition of the chemicals in the preparation of the growth solution leads to the formation of iron oxide nanoparticles in different shapes including sphere, oval, flower, pin and star; according to a preferred embodiment of the invention, the polymer may be poly (maleic anhydride-alt-1-octadecene). In certain embodiments, the concentration of $Ag^+$ is less than about 80 uM. In the present methods, silver nanoparticles initiate the growth of gold shell onto the polymer layer on the iron oxide nanoparticles in the presence of several shape-controlling agents. By controlling the amount of shape agents, the speed of gold deposition and the surface density of silver on iron oxide nanoparticles, iron oxide-gold core-shell nanoparticles are obtained.

The iron oxide-gold core-shell nanoparticles of the invention (in particular, the anisotropic nanoparticles) can be used in material and medical applications. The ovals, flowers, stars and pins show 30 to 50 times stronger surface enhanced Raman scattering activities than conventional iron oxide-gold core-shell spheres (FIG. 8). This demonstrates that the anisotropic nanoparticles are very promising for biosensing and medical detection. The surface enhanced Raman scattering signals were collected from QSY 21-adsorbed iron oxide-gold core-shell nanoparticles. The stars and pins show strong photothermal effects under exposure to near infrared laser (FIG. 9). They are 50 times better than gold nanorods, one of the major conventional photothermal contrast agents (FIG. 10). The nanoparticles of the invention are therefore useful as photothermal contrast agents, e.g., as agents for photothermal therapy. Thus, anisotropic iron oxide-gold core-shell nanoparticles have great potential for photothermal therapy of cancer and other diseases.

The invention also relates to an application of the IO-Au NPs (particularly anisotropic NPs), which is capture and detection of cancer cells in whole blood. Cancer cells in blood, refereed to as circulating tumor cells (CTCs), are malignant cells that have exfoliated from a primary tumor and circulate in the bloodstream of cancer patients. They are a hallmark of invasive behavior of cancer, responsible for the development of metastasis [20]. Their detection can provide a powerful tool for cancer prognosis, assessment of tumor stage, monitoring of therapeutic response, and ultimately aiding in optimization of personalized treatment for patient with metastatic cancer. In addition, CTCs have been found in blood during early stages of tumorigenesis [21]. Therefore, sensitive and specific detection of CTCs can also help in early detection of cancer, and thus preventing metastasis.

CTC detection, however, is extremely challenging because the number of CTCs in the blood of cancer patients is very low, as few as one cell per 10 million leukocytes (white blood cells, WBCs) and 5 billion erythrocytes (red blood cells, RBCs) [21]. It requires highly specific and sensitive techniques to identify and capture rare cancer cells with high efficiency. During the last two decades, a variety of enrichment and detection techniques have been developed, making significant progress in CTC detection[22-25]. A general strategy, including the only technique approved by U.S. Food and Drug Administration (FDA) for clinical utilization (the CellSearch system [26]), is to initially separate the tumor cells from abundant blood cells using isolation methods such as density gradient centrifugation, size-based filtration and immunomagnetic separation. After purification, CTCs are collected, processed and analyzed based on nucleic acid- or protein-based tumor markers. Consequently, multiple procedural preparations are needed, often leading to the loss of the rare cells and the decay of molecular biomarkers. In addition, substantial human intervention, high cost, and long turnaround time are also significant barriers.

Dye-adsorbed metal NPs, referred to as surface enhanced Raman scattering nanoparticles (SERS NPs), have emerged as a new type of biological labels for cancer detection during the last decade[27]. The rationale is that SERS NPs have exceptional detection sensitivity and specificity. The enhancement of the Raman signals of the dye by the supporting metal NPs can be as much as $10^{14}$ to $10^{15}$ [28], thus facilitating the detection down to the single molecule or single particle level. Different from the fluorescence technique, SERS provides sharp fingerprint signals that are specific to the adsorbed Raman reporters, allowing molecular detection in complex biological milieu. In 2008, Sha et al. reported the use of gold (Au) SERS NPs in combination with magnetic beads to detect CTCs in whole blood using CTC-mimic breast cancer cells, with a limit of detection (LOD) of 50 cells per mL of blood [29]. Recently, Wang et al. reported the detection of head and neck cancer cells in the presence of white blood cells using SERS Au NPs and density centrifugation, with a LOD of 5-50 cells per mL of blood [30]. The lack of magnetic properties of current SERS NPs for CTC detection requires that additional steps be taken to isolate and enrich the rare tumor cells. Correspondingly, additional magnetic particles or other separation techniques such as density centrifugation have to be used in order to isolate and enrich the rare tumor cells from abundant blood cells. This leads to limited detection sensitivity because of the cell loss during multiple sample preparations. In addition, magnetic particles currently used for CTC isolation are mainly the micron-sized magnetic beads. Microparticles have a low surface-to-volume ratio, which leads to a lower binding affinity compared to NPs. Microparticles are more likely to aggregate or precipitate in whole blood due to gravitational sedimentation. In addition, microparticles are not efficient for cell separation in whole blood because the high viscosity and high cell density of blood milieu prevent efficient particle contact with the cell surface receptors. Thus, pre-treatment of blood samples such as dilution with buffers, centrifugation to separate plasma and lysis of the red blood cells is generally needed to increase the binding capability of the beads to cell surface antigens. The invention provides new assays for high sensitivity detection of rare epithelial cancer cells in unprocessed blood based on innovative application of the magnetic-optical hybrid NPs.

Methods of Making Anisotropic Iron Oxide-Gold Core-Shell Nanoparticles

In one aspect, the invention provides a method for the synthesis of magnetic-optical iron oxide-gold core-shell nanoparticles in different shapes. The method comprises (a) preparation of silver-adsorbed iron oxide nanoparticles and (b) growth of gold shell onto the silver-adsorbed iron oxide nanoparticles to form iron oxide-gold core-shell nanoparticles such as nanospheres, nanoovals, nanoflowers, nanopins, nanohexagons or nanostars.

An exemplary method for the preparation of nanoparticles is shown in FIG. 1, in which, in a first step, diamminesilver ions (which can be prepared by mixing ammonia with silver nitrate) are adsorbed onto polymer-coated superparamagnetic iron oxide (magnetite or maghemite) nanoparticles, and are then (optionally after removal of unabsorbed diamminesilver ions, e.g., by centrifugation) reduced with sodium borohydride to form silver-adsorbed iron oxide nanoparticles. The iron oxide nanoparticles from 10 to 50 nm in diameter may be used to prepare the core-shell nanoparticles. After optional centrifugation to remove solid silver nanoparticles (which may be produced by reduction of free silver ions in solution), the silver-adsorbed iron oxide nanoparticles are dispersed in water and will be used as the seed to induce the growth of gold shell on the iron oxide nanoparticles.

In a second step, a growth solution is prepared by adding cetyltrimethylammonium bromide into water and heating to dissolve. The solution is cooled, followed by addition of chloroauric acid, gold (III) and silver nitrate. Then a reducing agent such as ascorbic acid is added to reduce gold (III) to gold (I) ions, and the silver-adsorbed IO NPs are added, which leads to the formation of iron oxide-gold core-shell nanoparticles. The growth of the core-shell nanoparticles will typically be complete within 2 hours.

The growth of the gold shell can be made by introducing small silver (Ag) nanoparticles (NPs) (2-5 nm) on the polymer rather than Au seeds or no seeds (as described in previously-reported methods). We have found that small Ag seeds can be used as nucleation sites because the Ag-adsorbed IO NPs can by formed without aggregation by the reduction of the purified $Ag(NH_3)_2^+$-adsorbed IO NPs, without forming Ag seeds in solution that will lead to the formation of solid Au NPs. Silver has the same crystal structure as gold, with nearly 100% lattice matching, and advantageously has no capping molecules on its surface. As a result, gold can be uniformly deposited onto the silver nucleation sites. Another advantage of this method over previous approaches is that deposition of Au atoms onto IO NPs can be achieved by reduction of $HAuCl_2$ ($Au^+$) with mild reducing agent ascorbic acid, instead of direct reduction of $HAuCl_4$ ($Au^{3+}$) with strong reducing agents which could lead to the formation of solid Au NPs. The formation of IO-Au NPs was usually accomplished within 2 hours. This rapid process is due to the surface-catalyzed reduction of $Au^+$ to $Au^0$ by ascorbic acid. However, reduction of $Au^+$ to $Au^0$ by ascorbic acid in solution is extremely slow, taking more than 24 hours. Thus, the use of $Au^+$ ions as Au precursors leads to high purity IO-Au core-shell NPs.

The shape of the nanoparticles can be controlled by the concentrations of ascorbic acid and silver nitrate in the growth solution, diamminesilver ions in the preparation of silver-adsorbed iron oxide nanoparticles and the duration between the additions of silver nitrate, ascorbic acid and silver-adsorbed iron oxide nanoparticles into the growth solution.

In certain embodiments, a polymer is used to form a polymer gap to overcome the crystal mismatching between IO and Au NPs. In a preferred embodiment, the polymer may be poly(maleic anhydride-alt-1-octadecene).

Superparamagnetic iron oxide nanoparticles may be purchased from Ocean Nanotech (Springdale, Ak.). The surface of the nanoparticles (SHP series) is a polymer layer composed of amphiphilic poly(maleic anhydride-alt-1-octadecene) that provides negatively charged carboxylic groups for the adsorption of positively charged ions in addition to interacting with oleic acid on the as-prepared IO NPs to make IO NPs water soluble. The nanoparticles are used as they are. They are referred to as SHP iron oxide nanoparticles. The oleic acid-coated iron oxide nanoparticles may be purchased from any other source or made by any of existing methods as long as the nanoparticles are capped with oleic acid. The nanoparticles are then coated with poly(maleic anhydride-alt-1-octadecene) according to the method by Shtykova et al. [31].

The process of the invention yields uniform iron oxide-gold core-shell nanoparticles in different shapes, such as sphere, oval, flower, pin and star shapes, depending on the growth conditions (FIGS. 2-6). The nanoparticles show optical absorption in visible (sphere, oval and flower) or near infrared (pin and star) regions. The nanoparticles are magnetic and can be separated from solution in the presence of external magnetic field. Quantitative measurement with a vibration magnetometer showed the hybrid NPs are superparamagnetic, similar to the iron oxide core (FIG. 7).

The conditions for formation of the silver-adsorbed iron oxide nanoparticles and for deposition of gold onto the silver-adsorbed iron oxide nanoparticles to form iron oxide-gold core-shell nanoparticles can be modified to yield iron oxide-gold core-shell nanoparticles in each shape with different core sizes by using SHP iron oxide nanoparticles with different sizes. In the Examples herein, SHP 25, which has diameter of 25 nm, can be used. Iron oxide from 10 to 50 nm may also be used to prepare the core-shell nanoparticles. The method may be further adjusted to make iron oxide-gold core-shell nanoparticles in different shell thickness by changing the amount of silver-adsorbed iron oxide in the growth solution. In the Examples herein, 22 microliter of seed is used. By changing the seed amount from 2 to 35 microliter, the hybrid nanoparticles with different shell thickness may be obtained.

The present methods may be used for large scale synthesis of iron oxide-gold core-shell nanoparticles. In the description of the Examples, 1.5 milliliter of nanoparticles is prepared. By proportionally increasing the chemical amount, nanoparticles may be prepared in larger quantities.

Methods of Detecting Analytes

In another aspect, the invention provides a method of detecting an analyte or a cell in a sample, the method comprising:

contacting the sample with an anisotropic iron oxide-gold core-shell nanoparticle capable of specific binding with the analyte or cell; and detecting the presence of the anisotropic iron oxide-gold core-shell nanoparticle, thereby detecting the analyte or cell.

The anisotropic iron oxide-gold core-shell nanoparticles of the invention can be used for detection of analytes (including, e.g., antigens, cells, and the like) in a sample (such as a biological sample, including fluids, tissues, and the like).

In certain embodiments, anisotropic iron oxide-gold core-shell nanoparticle is a nanooval. In certain embodiments, the analyte or cell is a cancer cell, such as a circulating tumor cell. In certain embodiments, the anisotropic iron oxide-gold core-shell nanoparticle is conjugated to an antibody capable of specifically binding the analyte or cell. In certain embodiments, the method includes the step of magnetically separating the anisotropic iron oxide-gold core-shell nanoparticle bound to the analyte or cell from the sample.

In general, the anisotropic iron oxide-gold core-shell nanoparticles can be surface-modified to specifically bind to an analyte; detection of the bound nanoparticle permits detection (and optionally quantitation) of the analyte. Separation of the nanoparticle bound to the analyte is facilitated by the magnetic core of the nanoparticle, which permits the use of magnets to separate the nanoparticle from the sample (e.g., a fluid), thereby simplifying detection and removing potentially interfering substances.

By attaching a member of specific binding pair to the surface of the nanoparticle of this invention, the nanoparticle can bind specifically to the complementary member of the specific binding pair in solution or in a sample, thereby permitting isolation or detection of the complementary member of the specific binding pair in the solution or in the sample. Examples of specific binding pairs include antibody-antigen, binding protein-ligand (e.g., avidin with biotin), a nucleic acid strand with a complementary nucleic acid, and the like. Examples of specific binding pairs are known in the art and can be selected by a person or ordinary skill in the art based on factors such as binding affinity, ease of preparation or isolation, and the like.

The iron oxide-gold core-shell nanoparticles of the invention can be conjugated to an antibody or other specific binding moiety according to methods known in the art or described herein. For example, antibodies (such as anti-EpCAM or anti-HER monoclonal antibodies) can be coupled to the surface of a nanoparticle of the invention by reaction of carboxyl groups on the surface of the nanoparticles with primary amines on antibodies. This reaction can be facilitated using standard peptide coupling reagents and techniques. The antibody can be attached to the nanoparticle through a spacer or linker arm if desired.

In certain embodiments, the nanoparticle, once bound to the analyte, is separated from the sample, e.g., using a magnet. The nanoparticle-analyte complex can be centrifuged and/or washed to remove potentially interfering substances (such as unbound nanoparticle, unbound analyte, cellular debris, etc.). The presence of the nanoparticle can then be detected using a variety of means, including visible, UV/IR, or Raman spectroscopy. Suitable dye molecules can be adsorbed on the nanoparticles to provide a detectable label; for example, a Raman-active dye can be adsorbed on to the nanoparticle to permit detection by Raman spectroscopy of the dye in the nanoparticle-analyte complex.

EXAMPLES

Example 1

Preparation of Iron Oxide-Gold Core-Shell Nanospheres 20 microliters of 1 molar (M) ammonia was added to 1 milliliter of 10 millimolar silver nitrate. The mixture was vortexed for two to three minute. Then, 10 microliter of this solution was added to 100 microliter of 1 milligram per milliliter SHP 25 iron oxide nanoparticles and the mixture was vortexed for 30 minutes. Then, 400 microliter water was added and the solution was centrifuged (12,000 rpm, 16 minutes). The supernatant was discarded and the pellet was resuspended in 0.5 milliliter water. Then, 100 microliter of 10 millimolar sodium borohydride was added and the mixture was vortexed for 40 minutes, followed by centrifugation (12,000 rpm, 16 minutes). The supernatant was discarded and the pellet resuspended in 0.5 milliliter water to form silver-adsorbed iron oxide nanoparticles.

54 milligram cetyltrimethylammonium bromide was added to 1.5 milliliter water. The solution was heated to 50 to 60 degree Celsius (° C.) with stirring. After the solid dissolved, the solution was cooled and put in a 23 degree celsius water bath. Under constant stirring, 60 microliter of 1 millimolar chloroauric acid was added. After 1 minute, 23 microliter of 40 millimolar ascorbic acid was added. After 1 minute, 22 microliter of silver-adsorbed iron oxide nanoparticles was added and iron oxide-gold nano spheres formed within 2 hours. The nanoparticles were purified by centrifugation (12,000 rpm, 10 minutes) and resuspended in water. The nanoparticles showed purple color in solution (FIG. 2). They exhibited surface plasmon absorption around 550 nm and average 55 nm in size. They can be separated from solution after exposure to an external permanent magnet.

Preparation of Iron Oxide-Gold Core-Shell Nanoovals 20 microliter of 1 molar ammonia was added to 1 milliliter of 10 millimolar silver nitrate. The mixture was vortexed for two to three minute. Then, 10 microliter of this solution was added to 100 microliter of 1 milligram per milliliter SHP 25 iron oxide nanoparticles and the mixture was vortexed for 30 minutes. Then, 400 microliter water was added and the solution was centrifuged (12,000 rpm, 16 minutes). The supernatant was discarded and the pellet was resuspended in 0.5 milliliter water. Then, 100 microliter of 10 millimolar sodium borohydride was added and the mixture was vortexed for 40 minutes, followed by centrifugation (12,000 rpm, 16 minutes). The supernatant was discarded and the pellet was resuspended in 0.5 milliliter water to form silver-adsorbed iron oxide nanoparticles.

54 milligram cetyltrimethylammonium bromide was added to 1.5 milliliter water. The solution was heated to 50 to 60 degree celsius with stirring. After the solid dissolved, the solution was cooled and put in a 23 degree celsius water bath. Under constant stirring, 60 microliter of 1 millimolar chloroauric acid was added. After 5 minutes, 120 microliter of 1 millimolar silver nitrate was added. After 15 minutes, 23 microliter of 40 millimolar ascorbic acid was added. After 5 minutes, 22 microliter of silver-adsorbed iron oxide nanoparticles was added and iron oxide-gold nanoovals formed within 2 hours. The nanoparticles were purified by centrifugation (12,000 rpm, 10 minutes) and resuspended in water. The nanoparticles show blue color in solution (FIG. 3). They exhibit surface plasmon absorption around 580 nm and average 60 nm from the tip to base and 50 nm along the base. They are separated from solution after exposure to an external permanent magnet.

Preparation of Iron Oxide-Gold Core-Shell Nanoflowers 20 microliter of 1 molar ammonia was added to 1 milliliter of 10 millimolar silver nitrate. The mixture was vortexed for two to three minute. Then, 100 microliter of this solution was added to 100 microliter of 1 milligram per milliliter SHP 25 iron oxide nanoparticles and the mixture was incubated overnight. Then, 400 microliter water was added and the solution was centrifuged (12,000 rpm, 16 minutes). The supernatant was discarded and the pellet was resuspended in 0.5 milliliter water. Then, 100 microliter of 10 millimolar sodium borohydride was added and the mixture was vortexed for 40 minutes, followed by centrifugation (12,000 rpm, 16 minutes). The supernatant was discarded and the pellet was resuspended in 0.5 milliliter water to form silver-adsorbed iron oxide nanoparticles.

54 milligram cetyltrimethylammonium bromide was added to 1.5 milliliter water. The solution was heated to 50 to 60 degree celsius with stirring. After the solid dissolved, the solution was cooled and put in a 23 degree celsius water bath. Under constant stirring, 60 microliter of 1 millimolar chloroauric acid was added. After 5 minutes, 90 microliter of 1 millimolar silver nitrate was added. After 5 minutes, 23 microliter of 40 millimolar ascorbic acid was added. After 5 minutes, 22 microliter of silver-adsorbed iron oxide nanoparticles was added and iron oxide-gold nanoovals formed within 2 hours. The nanoparticles were purified by centrifugation (12,000 rpm, 10 minutes) and resuspended in water. The nanoparticles show blue color in solution (FIG. 4). They exhibit surface plasmon absorption around 610 nm and average 100 nm. They are separated from solution after exposure to an external permanent magnet.

Preparation of Iron Oxide-Gold Core-Shell Nanostars 20 microliter of 1 molar ammonia was added to 1 milliliter of 10 millimolar silver nitrate. The mixture was vortexed for two to three minute. Then, 10 microliter of this solution was added to 100 microliter of 1 milligram per milliliter SHP 25 iron oxide nanoparticles and the mixture was vortexed for 30 minutes. Then, 400 microliter water was added and the solution was centrifuged (12,000 rpm, 16 minutes). The supernatant was discarded and the pellet was resuspended in 0.5 milliliter water. Then, 100 microliter of 10 millimolar sodium borohydride was added and the mixture was vortexed for 40 minutes, followed by centrifugation (12,000 rpm, 16 minutes). The supernatant was discarded and the pellet was resuspended in 0.5 milliliter water to form silver-adsorbed iron oxide nanoparticles.

54 milligram cetyltrimethylammonium bromide was added to 1.5 milliliter water. The solution was heated to 50 to 60 degree celsius with stirring. After the solid dissolved, the solution was cooled and put in a 23 degree celsius water bath. Under constant stirring, 60 microliter of 1 millimolar chloroauric acid was added. After 5 minutes, 120 microliter of 1 millimolar silver nitrate was added. After 15 minutes, 38 microliter of 40 millimolar ascorbic acid was added. After 5 minutes, 22 microliter of silver-adsorbed iron oxide nanoparticles was added and iron oxide-gold nanooovals formed within 2 hours. The nanoparticles were purified by centrifugation (12,000 rpm, 10 minutes) and resuspended in water. The nanoparticles show blue color in solution (FIG. 5). They exhibit surface plasmon absorption around 580 nm and average 60 nm from the tip to base and 50 nm along the base. They are separated from solution within 3-6 hours after exposure to an external permanent magnet.

Preparation of Iron Oxide-Gold Core-Shell Nanopins 20 microliter of 1 molar ammonia was added to 1 milliliter of 10 millimolar silver nitrate. The mixture was vortexed for two to three minute. Then, 10 microliter of this solution was added to 100 microliter of 1 milligram per milliliter SHP 25 iron oxide nanoparticles and the mixture was vortexed for 30 minutes. Then, 400 microliter water was added and the solution was centrifuged (12,000 rpm, 16 minutes). The supernatant was discarded and the pellet was resuspended in 0.5 milliliter water. Then, 100 microliter of 10 millimolar sodium borohydride was added and the mixture was vortexed for 40 minutes, followed by centrifugation (12,000 rpm, 16 minutes). The supernatant was discarded and the pellet was resuspended in 0.5 milliliter water to form silver-adsorbed iron oxide nanoparticles.

54 milligram cetyltrimethylammonium bromide was added to 1.5 milliliter water. The solution was heated to 50 to 60 degree celsius with stirring. After the solid dissolved, the solution was cooled and put in a 23 degree celsius water bath. Under constant stirring, 60 microliter of 1 millimolar chloroauric acid was added. After 5 minutes, 120 microliter of 1 millimolar silver nitrate was added. After 15 minutes, 150 microliter of 40 millimolar ascorbic acid was added. After 5 minutes, 22 microliter of silver-adsorbed iron oxide nanoparticles was added and iron oxide-gold nanopins formed within 2 hours. The nanoparticles were purified by centrifugation (12,000 rpm, 10 minutes) and resuspended in water. The nanoparticles show blue color in solution (FIG. 6). They exhibit surface plasmon absorption around 580 nm and are average 60 nm from the tip to base and 50 nm along the base. They can be separated from solution after exposed to an external permanent magnet.

Example 2

Here we report a new assay for high sensitivity detection of rare epithelial cancer cells in unprocessed blood based on innovative application of dually functional magnetic-optical hybrid NPs. We developed novel iron oxide-gold (IO-Au) core-shell NPs in oval shapes with combined superparamagnetic properties and SERS activities. The highly integrated IO-Au SERS NPs allow on-line magnetic separation and SERS detection of cancer cells in whole blood, with the detection sensitivity down to 1-2 cells per mL of blood.

Materials and Methods

Reagents. All chemicals were purchased from Sigma-Aldrich unless specified. QSY21 was purchased from Life Technologies (Grand Island, N.Y., USA). Anti-epithelial cell adhesion molecules (anti-EpCAM) and anti-human epidermal growth factor receptors (anti-HER2) monoclonal antibodies were purchased from AbCAM (Cambridge, Mass., USA). Carboxypoly(ethylene)-thiol (HOOC-PEG-SH, MW 5000) and methoxy-PEG-thiol (mPEG-SH, MW 5000) were purchased from Laysan Bio, Inc (Arab, Ala., USA). SK-BR-3 cells were purchased from ATCC (Manassas, Va., USA). Human whole blood was purchased from Research Blood Components, LLC. IO NPs (SHP 25) were obtained from Ocean Nanotech (Springdale, Ark., USA).

Synthesis and Characterization of IO-Au Nano-Ovals (NOVs).

IO-Au NOVs were synthesized using a seed-mediated growth method with modifications. First, 10 µL of 10 mM diamminesilver ions ($Ag(NH_3)_2^+$), which were prepared by mixing ammonia with silver nitrate ($AgNO_3$), were added to 100 µL of 1 mg/mL negatively charged polymer-coated IO NPs and stirred for 30 min. The $Ag^+$-adsorbed IO NPs were purified by centrifugation (10,000 rpm, 8 min) and reconstituted with 0.25 mL water, followed by addition of 100 µL of 10 mM sodium borohydride ($NaBH_4$) to form Ag-decorated IO NPs. After 40 min, the Ag-decorated IO NPs were purified by three times centrifugations and washings and redispersed in 500 µL water.

Second, 1.5 mL of growth solution containing 0.4 mM chloroauric acid ($HAuCl_4$), 0.1 M cetyl trimethylammonium bromide (CTAB) and 0.08 mM $AgNO_3$ were prepared, followed by addition of 23 µL of 40 mM ascorbic acid (AA). Then, 22 µL of the Ag-decorated IO NP solution was injected and the solution changed to a purple color within a few minutes, indicating the growth of IO-Au NOVs. The absorption spectra of the NPs were measured using a VIS-NIR absorption spectrometer (Ocean Optics, Dunedin, Fla.). The magnetic properties were measured using a vibration sample magnetometer (Dexing Magnets, China). The size and morphology of the NPs were examined with a JEM1200EX II TEM (JEOL Ltd, Tokyo, Japan).

Preparation and Characterization of Antibody-Conjugated IO-Au SERS NOVs.

Firstly, 50 µL, 0.1 mM QSY21 was added to 1 mL of 0.1 nM IO-Au nanoovals (NOVs) (QYS 21/IO-Au=50,000). The mixture was vortexed in the dark for 15 min to allow the adsorption of the dye onto the NPs. This was followed by addition of 20 µL, 0.05 mM carboxy-poly(ethylene)-thiol (HOOC-PEG-S, MW 5000). The bifunctional PEG was attached to the NPs via Au—S bonds. After vortexing for 20 min, 10 µL of 0.05 mM methoxy-PEG (mPEG-SH, MW 5000) was added to saturate the surface of the NPs. The mixture was vortexed for 1 hr in the dark at room temperature. The functionalized IO-Au SERS NOVs were centrifuged and washed for 3 times (10,000 rpm, 10 minutes) to separate unbound molecules. The NPs were redispersed in 100 µL of pH 5.5 MES buffer for ligand conjugation.

To conjugate anti-epithelial call adhesion molecules (anti-EpCAM) or anti-human epidermal growth factor receptor (anti-HER) monoclonal antibodies to the IO-Au SERS NOVs, 3 mg 1-Ethyl-3-(3-dimethylaminopropyl)carbodiimide (EDC) and 3 mg sulfo-N-hydroxysuccinimide (sulfo-NHS) were added to 100 µL of 1 nM functionalized IO-Au SERS NOVs in pH 5.5 2-(N-morpholino) ethanesulfonic acid (MES) buffer. EDC and sulfo-NHS were used as cross-linking agents to couple carboxyl groups on the NPs to primary amines on antibodies. The mixture was vortexed for 15 min, followed by addition of 900 µL of PBS and centrifugation (10,000 rpm, 10 min). The NP pellet was redispersed in 200 µL of PBS, followed by the addition of 50 µL of 0.2 mg/mL antibodies. EDC and sulfo-NHS were used as cross-linking agents to couple carboxyl groups on the NPs to primary amines on antibodies. EDC reacts with —COOH groups to form O-acylisourea intermediates. The intermediate further reacted with sulfo-NHS to form semi-stable amine-reactive NHS-ester. The solution was vortexed for 2 hr at room temperature to complete the coupling reaction, and then stored at 4° C. Prior to use, the solution was centrifuged and washed. The antibody-conjugated IO-Au SERS NOVs were resuspended in 100 µL of PBS. Surface modification at each step was monitored by dynamic light scattering (DLS) measurement with a Particle Size Analyzer (Brookhaven Instruments Corp, NY, USA).

Construction of an Integrated System for on-Line Cell Isolation and Detection.

The major components of the system were a syringe pump (New Era Pump Systems Inc, Farmingdale, N.Y., USA), a quartz capillary (Inner diameter=100 µm, Outer diameter=10 µm), two cylindrical neodymium-iron-boron (Nd-FeB) magnets (K&J Magnetics Inc, Jamison, Pa., USA) and a portable Raman spectrometer (Enwave Optronics, Irvine, Calif., USA). The capillary was connected to the syringe with a plastic cap. The magnet-1 was 20 mm in diameter and 25 mm in thickness, with a surface field of 4800 Gauss (G). Its function is to separate and capture tumor cells under a high flow velocity (>3 cm/s). The magnet-2 was 0.2 mm in diameter and 3 mm in thickness, with a surface field of 500 G. Its function is to capture and confine the purified tumor cells at low flow velocity (<0.5 cm/s) to a fine region for SERS detection. It was fixed in a styrofoam holder. Both magnets were set up on the motorized XYZ stage of the Raman spectrometer. The capillary was tightly attached to the top side of the magnets. During cell capture and detection, the two magnets were attached to the system one at a time. The Raman spectrometer has an excitation laser with wavelength at 785 nm and adjustable power up to 250 mW. The laser beam spot is 200 µm at focus.

When the blood sample containing NP-labeled tumor cells is introduced to the system, the syringe pushes the sample to flow in the capillary. The tumor cells, but not free NPs and blood cells, are captured by the magnet 1 in the absence of the magnet 2. After separation, the magnet 1 was removed, and the cells are collected with PBS on-line and transferred to the magnet 2 where they are captured and detected by the Raman spectrometer.

Cell Culture and Labeling.

The antibody-conjugated nanoovals (see above) were tested for binding to SK-BR-3 breast cancer cells. Human breast cancer cells SK-BR-3 were cultured in RPMI 1640 medium with 10% fetal bovine serum (FBS) at 37° C. under 5% $CO_2$. To label cells with the antibody-conjugated IO-Au NPs, in a typical procedure, 10,000 SK-BR-3 cells in 1 mL of PBS were incubated with 5 pM anti-EpCAM/QSY21/IO-Au nanoovals and 5 pM anti-HER2/QSY21/IO-Au nanoovals for 30 min with gentle vortexing at room temperature. The cells were purified by repeated centrifugation and washing (1,500 rpm, 3 min). Unconjugated IO-Au SERS nanoovals were used as the control. The NP-treated cells were fixed with 4% paraformaldehyde. Cellular binding was examined by dark field imaging with an Olympus IX71 inverted microscope. Specific cellular bindings of the conjugated nanoovals were confirmed by the presence of dense nanoparticles on and/or in the cells, which in turn confirmed the successful ligand conjugation to the nanoparticles. Dark field images of cancer cells incubated with the antibody-conjugated nanoovals and unconjugated nanoovals are shown in FIGS. 12B and 12C.

Determination of Capture Efficiency.

To determine the capture efficiency of tumor cells by the magnet-1, SK-BR-3 cells were labeled with a cocktail of anti-EpCAM/IO-Au SERS NOVs and anti-HER2/IO-Au SERS NOVs, as described above. 1 mL of PBS containing 10,000 prelabeled cancer cells were introduced into the flow system and pumped through the capillary at a variety of flow velocities in the presence of magnet-1. Cells in a stock PBS solution were counted with a hemocytometer and then diluted with PBS to achieve the cell solution with the desired cell number. Uncaptured cells were quantified by cell counting with a hemocytometer. To determine the capture efficiency of the NPs by the magnet-1, 1 mL of 10 pM mPEG-stabilized IO-Au NOVs was introduced into the flow system and pumped through the capillary at a variety of flow velocities in the presence of magnet-1. The uncaptured NPs were quantified by absorption spectroscopy. The capture efficiency of tumor cells or NPs was presented as the percentage of trapped cells or NPs with respective to the loaded tumor cells or NPs.

Detection of Pre-Labeled SK-BR-3 Cells Spiked into Whole Blood.

SK-BR-3 cells were dispersed in PBS and labeled with a cocktail of 5 pM anti-EpCAM/QSY21/IO-Au NOVs and 5 pM anti-HER2/QSY21/IO-Au NOVs as described above. After purification and fixation, the cells were redispersed in PBS and counted with a hemocytometer. The cells were subject to a series of dilutions with PBS or human whole blood to make 1 mL solutions containing 10, 20, 50, 100, 250 or 500 cells. The sample was transferred to a 1.0 mL syringe and placed on the syringe pump. With the magnet-1 in position, the solution was pumped at 6 cm/s. After 10 min when all the solution was pumped, a vial containing fresh PBS was placed at the end of the capillary. 100 µL of PBS was pulled from the vial to resuspend the purified tumor cells while the magnet-1 was removed. Then, the magnet-2 was placed under the capillary and the tumor cells were pumped through the capillary at 0.2 cm/s. After 30 min when all the solution was pumped, the Raman spectrometer was turned on and the SERS spectrum was collected in real-time (10 ms per spectrum). The position of the magnet-2 was adjusted so that the tumor cells were all exposed to the laser beam, giving maximal signals. The focus of the laser was further adjusted to optimize the SERS signals. PBS or whole blood only was used as the negative control. The SERS spectrum with maximal intensity for each sample was used for quantitative studies. The spectrum was baseline corrected to subtract the SERS background (broad continuum emission) using a multi-segment polynomial fitting. The plot of SERS intensity at 1496 $cm^{-1}$ versus the cell number was fitted linearly using Origin 8. The limit of detection (LOD) was determined to be the cell concentration required to give a signal equal to the negative control plus three times that of the standard deviation of the negative control.

Detection of SK-BR-3 Cells Spiked into PBS and into Whole Blood.

1 mL of PBS or human whole blood containing 10, 20, 50, 100, 250 or 500 fixed SK-BR-3 cells was incubated with 5 pM anti-EpCAM/QSY21/IO-Au NOVs and 5 pM anti-HER2/QSY21/IO-Au NOVs for 30 min with gentle vortexing at room temperature. The mixture was then transferred into the flow system and subjected to isolation and detection using the procedures described above. PBS or whole blood containing the same concentration of conjugated NOVs but not tumor cells was used as the negative control. The plot of SERS intensity at 1496 cm$^{-1}$ versus the number of SKBR-3 cells was fitted linearly using Origin 8 and the LOD was calculated as the number of cells that gave a signal equal to the negative control plus three times that of the standard deviation of the negative control.

Results and Discussion

Synthesis and Properties of IO-Au NOVs

Anisotropic NPs are known to give much stronger enhancement of the electric field of incident light waves than spherical NPs [16]. Since Raman signals are proportional to the electric field of the light, the anisotropic NPs are better SERS substrates than spherical ones with similar size.

We have developed near infrared (NIR)-absorbing IO-Au NPs in pin shapes with 35-fold higher SERS activities than the conventional IO-Au nanospheres (see also Bhana S, Rai B K, Mishra S R, Wang Y, Huang X., "Synthesis and properties of near infrared-absorbing magnetic-optical nanopins" Nanoscale 4, 4939-4942 (2012)). Although the NPs allow SPR excitation with the NIR laser which benefits Raman enhancement, a potential concern is their photothermal effect that could change the Raman signals of the adsorbed reporters and damage cell structures. To overcome this limitation, we made anisotropic NPs with SPR shifted away from the wavelength of the Raman excitation laser without decreasing the SERS strength.

The hybrid NPs were made from negatively charged IO NPs (FIG. 11A) using the seed-mediated growth method described previously (Bhana S. et al. Nanoscale 4, 4939-4942 (2012)), but with 7 times lower amount of ascorbic acid in the growth solution. The TEM image showed that the IO-Au NPs were in oval shapes, with an average size (100 particles) of 60 nm along the long axis and 50 nm in short axis (FIG. 11B). The shell of Au was estimated to be 12 to 18 nm in thickness. The core-shell NPs exhibit a SPR peak at 590 nm (FIGS. 11C&D). The magnetic properties of the hybrid NPs were tested by the magnetic separation with external permanent magnets and quantitative magnetization measurement with a vibration sample magnetometer. When a permanent magnet was attached to a plastic vial containing the NOV solution, the particles were isolated from the solution, similar to the behavior of IO NPs (FIGS. 11E&F). The remaining liquid became colorless, indicating that the NOVs were indeed core-shell NPs. The magnetization measurement revealed that the hybrid NPs were superparamagnetic, similar to the IO core. The saturation magnetization of the core-shell NPs was 8 emu/g, which was 6 times lower than that of the IO core. This is not surprising because of the mass contribution from the diamagnetic Au that has a density 4 times higher than IO.

Preparation and Cell Labeling of Antibody-Conjugated IO-Au SERS NOVs

FIG. 12A shows the major steps for the preparation of antibody-conjugated IO-Au SERS NOVs targeting tumor cells. We used breast cancer as a model for the proof-of-concept studies. The NOVs were firstly coated with QSY21 quencher to form SERS-active NPs by electrostatic and electronic interactions. We used QSY21 as the Raman reporters because they do not have fluorescence background and they have highly delocalized pi-electrons that give strong SERS signals. To optimize the SERS NPs, we used excess reporter molecules to saturate the surface coating. Using absorption spectroscopy, we determined that approximately $1.2 \times 10^4$ QSY21 dye molecules were adsorbed on each particle. The as-prepared NOVs had a hydrodynamic diameter (HD) and zeta potential ($\zeta$) of 72 nm and 28 mV, respectively (Table 1).

TABLE 1

Characterization of the preparation of antibody-conjugated IO-Au SERS NOVs by DLS.

| | Hydrodynamic Diameter (nm) | Zeta Potential (mV) |
| --- | --- | --- |
| IO-Au NOVs | 72.0 ± 2.2 | 28.5 ± 0.5 |
| QSY21/IO-Au NOVs | 73.2 ± 2.7 | 24.8 ± 0.8 |
| HOOC-PEG/mPEG/QSY21/IO-Au NOVs | 96.1 ± 1.5 | −14.2 ± 1.2 |
| Anti-EpCAM/QSY21/IO-Au NOVs | 104.2 ± 3.1 | −10.1 ± 1.3 |
| Anti-HER2/QSY21/IO-Au NOVs | 103.5 ± 3.5 | −8.2 ± 1.2 |

The NOVs were positively charged because they were capped with a bilayer of the CTAB surfactant, which is similar to other NPs such as gold nanorods that were prepared in the same growth solution (Nikoobakht B, El-Sayed M A. "Evidence for bilayer assembly of cationic surfactants on the surface of gold nanorods", Langmuir 17(20), 6368-6374 (2001)).

Coating the NOVs with the reporter molecules did not significantly change the HD and. The QSY21-adsorbed NOVs were covalently linked with a mixture of HOOC-PEG-SH and mPEGSH (HOOC-PEG-SH/mPEG-SH=2) to introduce functional groups for ligand conjugation while stabilizing the SERS NPs. The PEG binding increased the particle size by 23 nm and decreased the surface charge of the NPs to −14 mV. Incorporation of neutral mPEG-SH molecules reduces the surface charge of the NPs and thus minimizes nonspecific binding to cancer cells (Huang X, Peng X, Wang Y et al. "A reexamination of active and passive tumor targeting by using rod-shaped gold nanocrystals and covalently conjugated peptide ligands." ACS Nano 4(10), 5887-5896 (2010)).

Antibodies were linked to NPs through amide bonds between the ligands and the heterofunctional PEG linkers via the standard EDC/sulfo-NHS activated coupling reaction (Huang X, et al., ACS Nano 4(10), 5887-5896 (2010)). The attachment of the antibodies increased the HD of the NPs by 5-8 nm and $\zeta$ by 2-5 mV. To increase detection sensitivity, we made conjugated NPs to target two markers, EpCAM and HER2. EpCAM is expressed on a vast number of epithelial tumor cells (Went P T, Lugli A, Meier S, et al. "Frequent EpCAM protein expression in human carcinomas." Hum. Pathol. 35, 122-128 (2004). HER2 is known to be overexpressed on nearly 30% of breast cancers. Both EpCAM and HER2 receptors are positive for SK-BR-3 cells.

Figure 12:
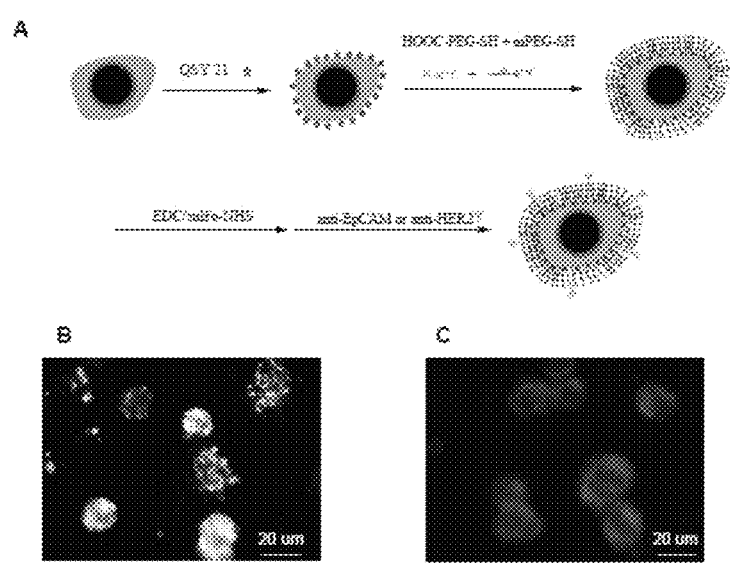
FIG. 12: (A) Schematic illustration of the preparation of antibody-conjugated IO-Au SERS NOVs; (B) Dark field image of SK-BR-3 cells incubated with a cocktail of anti-EpCAM/IO-Au SERS NOVs and anti-HER2/IO-Au SERS NOVs; and (C) Dark field image of SK-BR-3 cells incubated with unconjugated IO-Au SERS NOVs. The data show specific binding of antibody-conjugated IO-Au NOVs, but not the unconjugated ones, to the cancer cells.

To label the cancer cells, 10,000 SK-BR-3 cells were incubated with 5 pM anti-EpCAM/QSY21/IO-Au NOVs and 5 pM anti-HER2/QSY21/IO-Au NOVs in PBS at room temperature for 30 min with gentle shaking. Unconjugated NPs were used as the control. The NP-treated cells were separated from free NPs by gentle centrifugation and washing, followed by fixation. FIGS. 12 B&C show the dark field images of the cancer cells incubated with the antibody-conjugated NOVs and unconjugated NOVs, respectively. Specific cellular bindings of the conjugated NOVs were confirmed by the presence of dense NPs on and/or in the cells, which in turn confirmed the successful ligand conjugation to the NPs.

Figure 13:
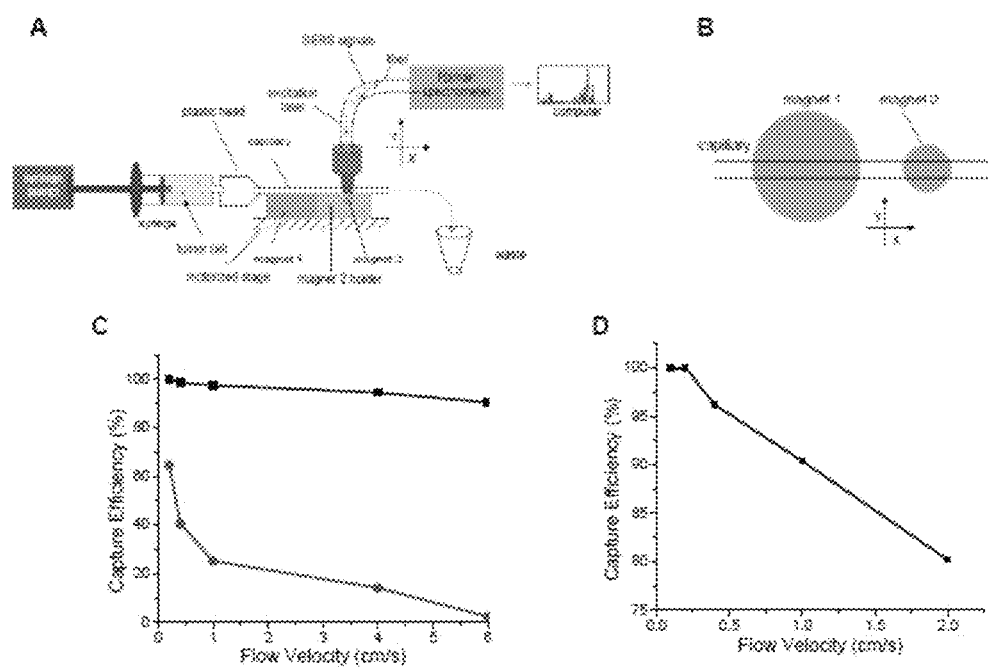
FIG. 13: (A) Schematic illustration of the integrated system for on-line magnetic capture and SERS detection of CTCs; (B) Top view of the magnets and the capillary in the flow system; (C) Plot of the capture efficiencies of pre-labeled SK-BR-3 cells (black) and free IO-Au NPVs (red) versus the flow velocity by the magnet 1; and (D) Plot of the capture efficiency of pre-labeled SK-BR 3 cells versus the flow velocity by the magnet 2.

Design and Construction of an Integrated System for on-Line Cell Capture and Detection Due to the scarcity of CTCs, a system that allows on-line isolation and detection is desirable in order to minimize cell loss. Magnetic separation under flow conditions has been shown to be an efficient way to capture NP-bound CTCs at appropriate flow rates without capturing free NPs. This is because the magnetic force is proportional to the number of bound NPs. The free NPs are more effectively removed by flow drag forces than the cells which contain a number of NPs. We constructed a syringe-pumped flow system and integrated it with permanents magnet to capture CTCs while separating unbound NPs and blood cells (FIGS. 13A&B). The pump, which is precisely programmable, works in a push/pull mode so that sample can flow through the capillary in both forward and backward directions. A strong and large magnet (magnet-1) was used to isolate and capture tumor cells with high efficiency. It allows cell isolation at high flow rates, enabling sample processing in a large volume within a short time. To minimize cell loss, the system was coupled with a high throughput portable Raman spectrometer so that purified and enriched cells can be directly detected on-line. During the detection, the tumor cells need to be confined within the laser beam and immobilized in the capillary so that they can be detected by the Raman spectrometer. Therefore, a second magnet (magnet-2) was used to capture and concentrate the purified cells to a fine region. The diameter of this magnet was designed to be the same as the diameter of the Raman laser beam at focus. This ensures that all the tumor cells captured by the magnet can be interrogated by the laser. Due to the small size, the magnetic field of the magnet-2 was much weaker than the magnet-1. This requires a much lower flow rate when the magnet-2 was used. We experimentally determined the optimal flow rate for the two magnets by examining the effects of flow velocities on the cell/NP capture efficiency.

FIG. 13C shows the capture efficiencies of pre-labeled SK-BR 3 cells and free IO-Au NOVs at different flow velocities by the magnet-1. The data show that the capture efficiency of the cells was much higher than that of the free NPs at the same flow velocity. The cell capture efficiency was 98% while that of the NPs were 25% at 1 cm/s. When the flow velocity was increased to 6 cm/s, the cell capture efficiency decreased to 90% while that of the NPs decreased to 2%. Thus, cancer cells can be efficiently captured at 6 cm/s without significant trapping of the free NPs. As for the small magnet-2, it was designed to capture tumor cells that had been separated from the free NPs by the magnet-1. Thus, the interference from free NPs is negligible.

FIG. 13D shows the capture efficiencies of pre-labeled cancer cells by the magnet-2 at different flow velocities. At 0.2 cm/s, the cell capture efficiency was 100%. The capture efficiency decreased to 90% at 1 cm/s and 80% at 2 cm/s, which were significantly lower than those by the magnet-1 due to the much weaker magnetic field gradient of the magnet-2. To ensure efficient capture efficiency, we used the flow velocity of 0.2 cm/s for the capture and confinement of the separated cancer cells for SERS detection.

Capture and Detection of Pre-Labeled Cancer Cells in Whole Blood

To validate the integrated system, we used SK-BR-3 cells labeled with IO-Au NOVs in advance. We spiked the pre-labeled SK-BR-3 cells into whole blood with a variety of concentrations (10-500 cells/mL) to determine the detection sensitivity. Each of the samples was introduced to the flow system and pumped through the capillary at the optimized flow velocity (6 cm/s, ~100 µL/min) in the presence of the magnet-1 to isolate the tumor cells from the blood cells. After the isolation, the cells were enriched and transferred back to the syringe by withdrawing a small amount of fresh PBS (100 uL) from a reservoir at the end of the capillary while the magnet-1 was removed. Then, the magnet-2 was attached and the cancer cells were pumped through the capillary again, but at a much lower flow rate (0.2 cm/s, ~3.5 uL/min) so that they were captured by the magnet-2. Real-time SERS measurement showed that the SERS signal intensity gradually increased with time, indicating the capture of tumor cells by the magnet. The signal intensity reached maximum when all the cells were confined and immobilized by the micromagnet.

The total assay time for each sample on the system was 45-60 min.

Figure 14:
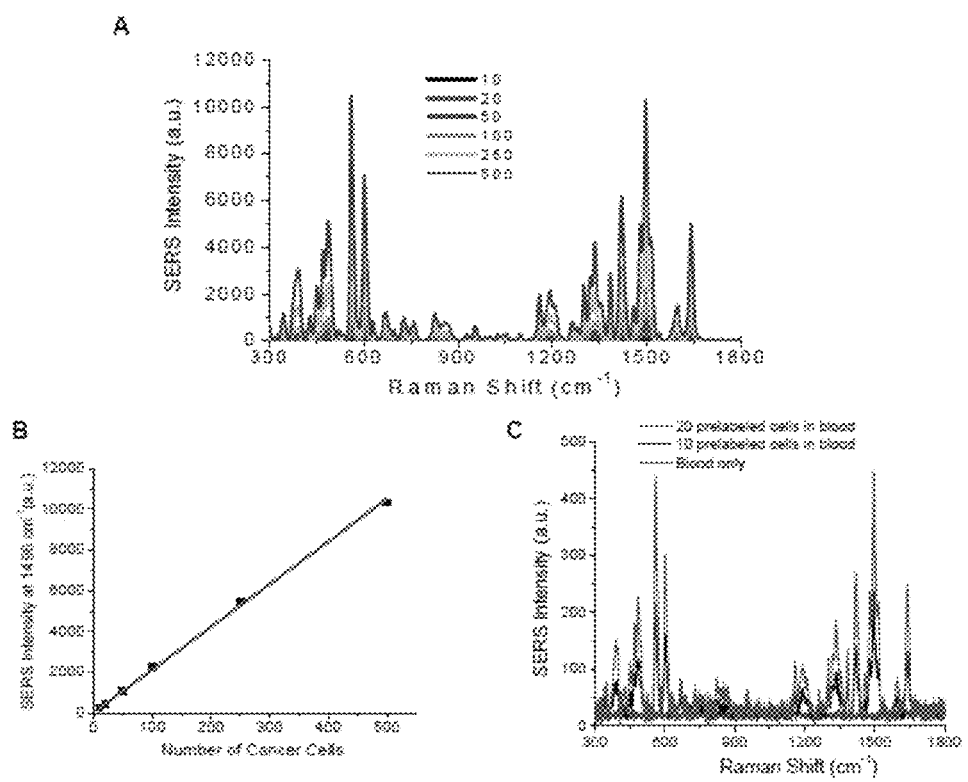
FIG. 14: Detection of prelabeled SK-BR-3 cells spiked into whole blood. (A) SERS spectra from different number of SK-BR-3 cells; (B) Plot of SERS signal intensity at 1496 cm$^{-1}$ versus the number of SK-BR-3 cells; (C) Comparison of SERS signals from 10 pre-labeled SK-BR-3 cells in the blood and signals from the blood only (the negative control). The calculated LOD was less than 1 cell/mL blood.

FIG. 14A shows the SERS spectra (averaged from three experiments) from different numbers of pre-labeled SK-BR-3 cells in 1 mL of whole blood. Each spectrum was collected within only 1 s. The experiment was not performed on cell concentration lower than 10 cells/mL due to the difficulty of spiking low number of cells accurately and reproducibly. The SERS signals increased proportionally as the cell number increased. A quantitative comparison was made using the peak at 1496 $cm^{-1}$, the strongest one in the whole spectral region (FIG. 14B).

The data shows excellent linear relationship between the signal intensity and the cell number, with correlation coefficient ($R^2$) of 99.8%. The blood (negative control) gave a background signal (averaged from three spectra from three blood control samples) of 17 a.u. that was 13 times lower than the signal intensity when 10 cells were present and 26 times lower than the signal intensity when 20 cells were present (FIG. 14C). Based on the linear correlation between the signal intensity and the cell number, and the background signals from the negative control, the LOD (the cell concentration required to give a signal equal to the negative control plus three times the standard deviation of the negative control) was calculated to be 0.2 cell/mL, less than 1 cell per mL of blood (99% confidence). This indicates that cancer cells labeled with duplexed TO-Au SERS NOVs can be captured under a flow condition via magnetic separation, followed by on-line SERS detection with high sensitivity.

Capture and Detection of Spiked Cancer Cells in PBS

The capability of the IO-Au NOVs and the integrated system for CTC capture and detection was firstly tested with the use of cultured breast cancer cells in PBS. In these studies, 1 mL of PBS containing varying number of fixed SK-BR-3 cells (10-500) was mixed with 5 pM (final concentration) anti-EpCAM/QSY21/IO-Au NOVs and 5 pM (final concentration) anti-HER2/QSY21/IO-Au NOVs. After incubation (30 min), the mixture was introduced to the flow system and CTCs were isolated, enriched and detected using the integrated system. PBS containing the NPs at the same concentration, but not cancer cells, was used as the negative control.

Figure 15:
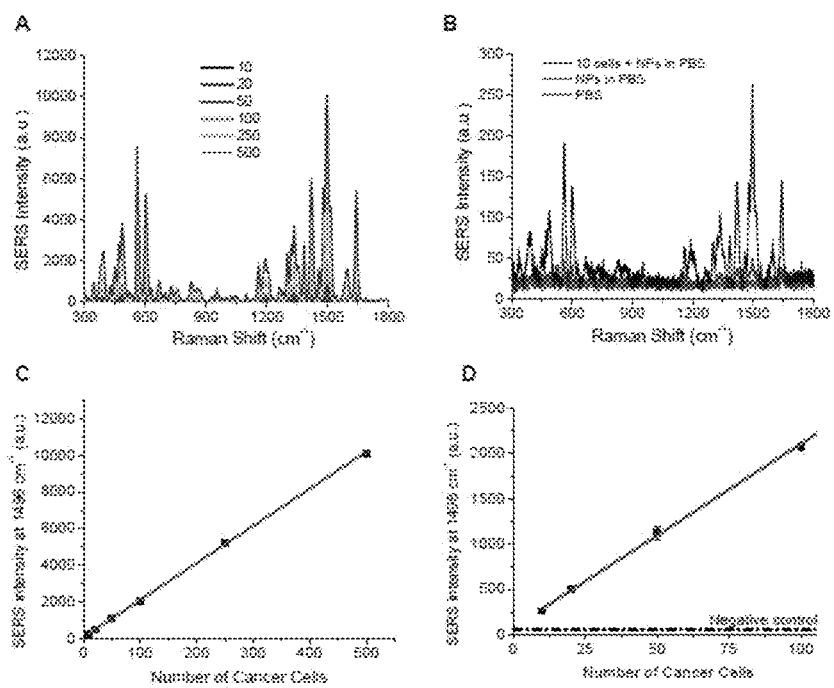
FIG. 15: Detection of SK-BR-3 cells spiked into PBS (phosphate-buffered saline). PBS continuing the specified numbers of SK-BR-3 cells was incubated with anti-EpCAM/IO-Au SERS NOVs for 30 minutes at room temperature, followed by on-line magnetic capture and SERS detection. (A) SERS spectra from different number of SK-BR-3 cells; (B) Comparison of SERS signal from NPs in PBS, 10 SK-BR-3 cells plus NPs in PBS, and signals from PBS only; (C) plot of SERS signal intensity at 1496 cm$^{-1}$ versus the number of SK-BR-3 cells from 10-500 cells; and (D) Enlarged plot of SERS signal intensity at 1496 cm$^{-1}$ versus the number of SK-BR-3 cells from 10-100. SERS signal intensity at 1496 cm$^{-1}$ from the NPs in PBS (the negative control) is shown for comparison. The calculated LOD was 1 cell/mL blood.

FIG. 15A shows the SERS spectra from different number of cells in 1 mL of PBS. Similar to pre-labeled cells, the signal intensity increased proportionally as the cell number increased. However, under this condition, free NPs were present in the sample. The SERS signal intensity at 1496 $m^{-1}$ from free NPs (the negative control) is 51 a.u., distinct from the PBS background signals (19 a.u.) (FIG. 15B). This indicates slight capture of the unbound NPs in the sample.

However, the effect from the captured free NPs for cell detection is not significant. As shown in FIG. 15B, the peak intensity increased to 267 a.u. with the presence of 10 cancer cells, which was more than 5 times stronger than that from the negative control. FIGS. 15C&D shows the quantitative relationship of SERS signal intensity at 1496 cm$^{-1}$ with the cell number in the whole range (10-500) and in the range of 10 to 100, respectively The data show excellent linear relationship between the signal intensity and the cell number ($R^2$: 99.8%). Based on the background signals from the negative control and the linear correlations shown in FIG. 15C, the LOD was calculated to be 1 cell per mL of PBS. This indicates that tumor cells can be efficiently captured and detected on-line with high sensitivity using IO-Au SERS NOVs.

Capture and Detection of Spiked Cancer Cells in Whole Blood

To mimic CTCs, we spiked cultured SK-BR-3 cells into human whole blood. To determine the detection sensitivity, 10, 20, 50, 100, 250 and 500 cancer cells were spiked into 1 mL whole blood. Each sample was incubated with 5 pM anti-EpCAM/QSY21/IO-Au NOVs and 5 pM anti-HER2/QSY21/IO-Au NOVs for 30 min with gentle shaking to allow the binding of conjugated IO-Au SERS NOVs to the cancer cells. After reaction, the sample was introduced to the flow system and CTCs were isolated, enriched and detected using the procedures described above. To examine the detection specificity, 1 mL whole blood without cancer cells was incubated with the same concentration of anti-EpCAM/QSY21/IO-Au NOVs and anti-HER2/QSY21/IO-Au NOVs for 30 min, followed by magnetic separation and SERS detection using the integrated system.

The free NPs in PBS were used as another control to investigate the nonspecific binding of the conjugated NPs to blood cells. A third control was the blood in the absence of the conjugated NPs and cancer cells.

Figure 16:
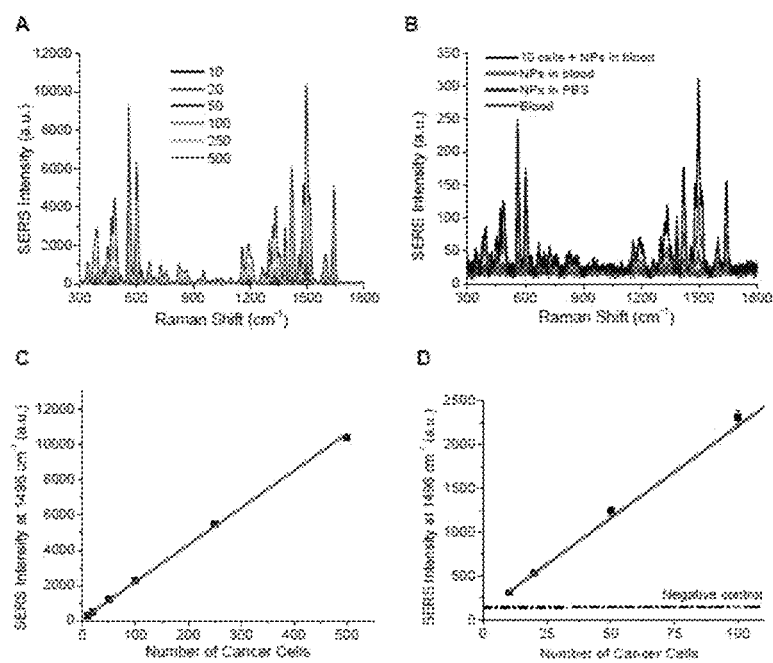
FIG. 16: Detection of SK-BR-3 cells spiked into whole blood. (A) SERS spectra from different number of SK-BR-3 cells; (B) Comparison of the SERS signals from NPs in PBS, NPs in blood, 10 SK-BR-3 cells plus NPs in blood and signals from blood only; (C) Plot of SERS signal intensity at 1496 cm$^{-1}$ versus the number of SK-BR-3 cells from 10-500 cells; and (D) Enlarged plot of SERS signal intensity at 1496 cm$^{-1}$ versus the number of SK-BR-3 cells from 10-100 cells. SERS signal intensity at 1496 cm$^{-1}$ from NPs in blood (the negative control) is shown for comparison. The calculated LOD was 1-2 cells/mL blood.

FIG. 16A shows the SERS spectra from different number of cells. Similar to the cancer cells spiked into PBS, the signal intensity increased proportionally as the cell number increased. A comparison of the averaged SERS signals from the three negative controls and the sample with low number of cancer cells (10 cells) was shown in FIG. 16B. At 1469 cm$^{-1}$, the signal intensity from blood only, free NPs in PBS, free NPs in blood, and 10 cells plus free NPs in the blood was 17, 52, 134 and 312 a.u., respectively. The weak signals from free NPs in PBS is due to the modest capture of the NPs by the permanent magnets, as described earlier. When the blood was incubated with the conjugated NPs, the signal intensity increased by 1.5-fold compared to that from free NPs in PBS. When the blood was spiked with 10 cells and incubated with the conjugated NPs, the signal intensity increased by 5-fold. These results indicate that the nonspecific binding of the conjugated NPs to blood cells is remarkably low, considering the fact that 1 mL of whole blood contains 10 million white blood cells and 5 billion red blood cells.

The SERS signal intensity at 1496 cm$^{-1}$ shows an excellent linear correlation with the cell number ($R^2$: 99.8%) (FIG. 16C). The negative control (free NPs in the blood) gave a background signal that was significantly lower than those from tumor cells (FIG. 16D). Based on the background signals from the free NPs and the linear correlation between the peak intensity and cell number, the LOD was calculated to be 1-2 cells per mL of blood. This is 25 times more sensitive than previous assay in which anti-EpCAM conjugated magnetic bead were used for magnetic separation and anti-HER2 conjugated SERS Au NPs were used for optical detection[29]. The improved detection sensitivity with our method is mainly due to the use of IO-Au hybrid NPs that not only capture the cancer cells but also detect them. Thus, cancer cells with either of HER2 and EpCAM markers or both can be simultaneously captured and detected.

In addition, the use of nanoscale magnetic NPs rather than magnetic bead enhances cell binding affinity [33]. Furthermore, the integration of magnetic separation, high throughput Raman detection and capillary flow system ensures that all cells captured by the magnet are detected.

Conclusion

Using CTC-mimic breast cancer cells as a model, we demonstrated for the first time the application of magnetic-optical hybrid NPs for dual capture/detection of CTCs in whole blood.

We developed compact IO-Au core-shell NPs in oval shapes with combined superparamagnetic properties and SERS activities. Our studies showed that novel IO-Au SERS NOVs combined with duplex targeting and an on-line capture and detection system allow high sensitivity detection of cancer cells in whole blood (LOD: 1-2 cells/mL blood), without tedious sample preparations and complex techniques. Our method provides a simple, rapid, quantitative and ultrasensitive technique for rare cell detection, which will make an important impact in the field of cancer medicine.

Multiplexed targeting can be readily achieved to further increase the detection sensitivity and specificity. Multiplexed IO-Au NOVs can be readily formed using different targeting ligands without changing the size and structure of the NPs. Thus, CTCs with different molecular markers can be simultaneously isolated and captured, followed by direct detection with SERS technology without use of additional probes. Secondly, multiplexed detection can be achieved for molecular profiling of biomarker expression using the same nanostructures. This can be done by simply changing the Raman tags to differentiate different markers such as epithelial-specific, tumor-specific, tumor stem cell and EMT markers. In addition, the on-line flow system can be readily translated into a microfluidic device for automated, rapid and point-of-care detection. Furthermore, a Raman microscope can be used for automated detection of CTCs at single cell resolution and for molecular profiling of biomarker expressions on single cells. The Raman microscope would eliminate the influence of cell debris in the cell suspension by measuring Raman signals from individual whole cell.

Example 3

In this Example, we modified the seed-mediated growth method to make a new anisotropic IO-Au nanostructure with very good quality and purity. By precisely controlling the temperature and key chemicals in the growth solution, we made monodisperse IO-Au NPs in hexagonal shapes. We further made the nanohexagons (NHGs) with different sizes by controlling the thickness of Au shell without changing the shape of the NPs. More importantly, we found that the NHGs showed remarkably higher SERS activities than conventional IO-Au NSs. The dual functional IO-Au NHGs will have important impact on biological separation, medical imaging and diagnostics.

Materials and Methods

Materials. All chemicals were purchased from Sigma-Aldrich unless specified. 25 nm superparamagnetic NPs were purchased from Ocean Nanotech (Cat Number: SHP 25, Springdale, Ark.). QSY21 was purchased from Life Technologies (Grand Island, N.Y.). Thiolated methoxy-poly (ethylene)glycol (mPEG-SH, MW 5000) was purchased from Laysan Bio, Inc (Arab, Ala.).

Synthesis of IO-Au core-shell NHGs. IO-Au core-shell IO-Au NHGs were synthesized by adapting our previously developed seed-mediated growth method (see Bhana S, Rai B K, Mishra S R, Wang Y, Huang X., "Synthesis and properties of near infrared-absorbing magnetic-optical nanopins" Nanoscale 4, 4939-4942 (2012)). Firstly, 10 μL of 10 mM diamminesilver ions ($Ag(NH_3)in_2^+$), which were prepared in advance by mixing 20 uL of 1 M ammonium hydroxide with 1 mL of 10 mM silver nitrate ($AgNO_3$) for 2-3 min, were added to 100 μL of 1 mg/mL SHP 25 nm IO NPs and stirred for 30 min. The $Ag(NH_3)_2^+$-adsorbed IO NPs were purified by centrifugation (10,000 rpm, 8 min) and reconstituted with 0.5 mL water, followed by addition of 100 μL of 10 mM sodium borohydride ($NaBH_4$) to form Ag-adsorbed IO NPs. After 40 min vortexing, the Ag-adsorbed IO NPs were purified by centrifugation and redispersed in 0.5 mL water. Next, 1.5 mL of growth solution containing 0.1 M cetyl trimethylammonium bromide (CTAB) and 0.4 mM chloroauric acid ($HAuCl_4$) was prepared and heated to 30° C., followed by sequential addition of 120 uL $AgNO_3$ and 25 μL of 40 mM ascorbic acid (AA). Then, 10 to 24 uL of the Ag-adsorbed IO NP solution was injected to initiate the growth of IO-Au NHGs with different shell thickness. The growth process took 1 h to complete. The NHGs were purified by 2 times of centrifugation and washing. To understand the growth mechanism, the effects of temperature, the amount of AA and $AgNO_3$ in the growth solution on the formation of hexagonal shape were studied by varying the temperature from 25 to 40° C., the amount of $AgNO_3$ from 0 to 240 uL and that of AA from 20 to 120 uL.

Characterization. The absorption spectra of the NPs were measured using an Ocean Optics VIS-NIR absorption spectrometer (Dunedin, Fla.). The size and morphology of the NPs were examined with a JEOL JEM1200EX II TEM (JEOL Ltd, Tokyo, Japan). The core-shell NPs were further confirmed by magnetic separation with a 12-tube magnet (Qiagen, Valencia, Calif.) Crystal structures of JO and JO-Au NPs were measured with a Bruker D8 advanced X-ray diffractometer.

SERS measurement. 50 uL, 0.1 mM QSY21 was added to 1 mL of 0.1 nM JO-Au NHGs with different shell thickness. The mixture was vortexed in dark for 15 min to allow the adsorption of the dye onto the NPs. This was followed by addition of 50 uL, 0.05 mM mPEG-SH. The mixture was vortexed for 1 h in dark at room temperature. The QSY21-adsorbed mPEG-stabilized JO-Au NHGs were centrifuged and washed for 3 times (10,000 rpm, 10 min) to separate free molecules. The NPs were redispersed in water for Raman measurement. The Raman spectra were collected on a microsense-L high performance Raman microscope (TSI, Inc. Shoreview, Minn.). The excitation laser wavelength is 785 nm. All spectra are collected with 25 mW laser power, is acquisition time and 10× objective.

Results and Discussion

Synthesis of IO-Au core-shell NPs is difficult because of the poor crystal lattice matching between JO and Au. For example, the lattice spacing of the (111) place for magnetite and maghemite is 4.85 and 4.82 Å, respectively. However, the lattice spacing of the same place for Au is 2.35 Å. Thus, direct deposition of Au on JO NPs usually leads to jagged coating. In our method, the magnetite NPs are coated with a very thin layer (~4 nm) of poly(maleic anhydride-alt-1-octadecene) (PMAO) that interacts with the oleic acid on the as-prepared JO NPs with the hydrophobic alkyl chain while exposing the hydrophilic carboxylate ions to anchor positively charged metal ions. The growth of the Au shell was made by introducing small silver (Ag) NPs (2-5 nm) on the polymer as the nucleation sites Ag has the same crystal structures of Au, with nearly 100% lattice matching. Thus, Au can be deposited onto the Ag nucleation sites and subsequent growth lead to uniform Au shell on the JO NPs. The deposition and anisotropic growth of Au shell were performed in a growth solution containing 0.1 M CTAB, 0.4 mM $AuCl_2^-$, 80 uM $AgNO_3$ and 0.67 mM AA. The AA concentration is 10% higher than that used in our previous studies to make NOVs (0.61 mM). The 0.67 mM AA was the initial final concentration in the growth solution. Since the first reduction step is the conversion of $AuCl_4^-$ to $AuCl_2$ by AA, about 0.21 mM AA existed in the growth solution theoretically when the Ag-adsorbed IO seed NPs were added. Another difference is the temperature of the growth solution. The synthesis of NOVs was conducted at 22° C. Here, we increased the temperature to and higher than 25° C. in order to promote the anisotropic growth of the NPs.

Figure 17:
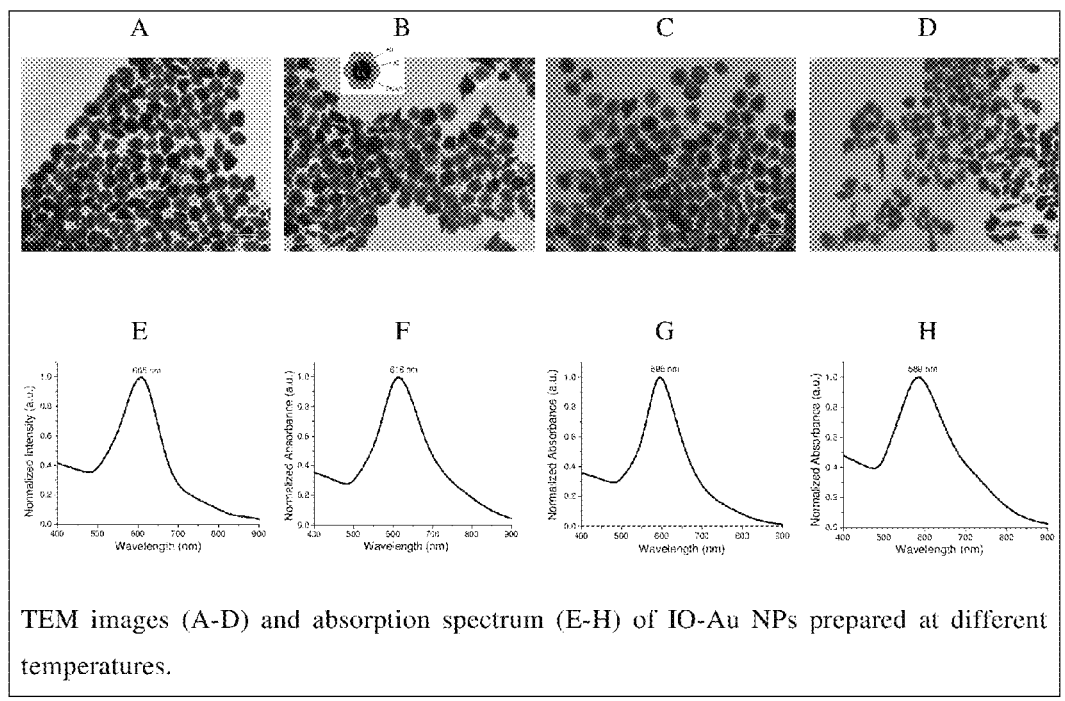
FIG. 17 shows typical transmission electron microscope (TEM) image and the corresponding absorption spectrum of the as-prepared TO-Au core-shell NPs prepared at 25° C., 30° C., 35° C. and 40° C. respectively. (A&E) 25° C., (B&F) 30° C., (C&G) 35° C. and (D&H) 40° C.

FIG. 17 shows typical transmission electron microscope (TEM) images and the corresponding absorption spectrum of the as-prepared IO-Au core-shell NPs prepared at 25° C., 30° C., 35° C. and 40° C. respectively. In these studies, 12 μL Ag-adsorbed IO NPs were used to initiate the growth of Au shell. At 25° C., the NPs contained a mixture of NOVs and NSs with small portion of NHGs, with a LSPR centered at 605 nm. When the temperature was increased to 30° C., a dramatic change occurred on the morphology of the NPs. About 90% of the NPs were in hexagonal shapes. Among those hexagonal NPs, over 85% NPs were within 72 nm±5 nm in the diagonal length (L in FIG. 17B inset). The LSPR wavelength of the IO-Au NHGs was 616 nm. When the temperature was increased to 35° C., the edge of the hexagon particles became blurry and thus the NPs had more rounded morphology. The LSPR blue shifted to 595 nm. At 40° C., the NPs contained multiple populations including hexagons, diamonds, pins, stars and hexagons. The hexagonal NPs were smaller than those formed at 30° C. Correspondingly, the absorption spectrum became broader and the LSPR further blue shifted to 589 nm. These studies showed that IO-Au core-shell NHGs with high quality were successfully prepared at the optimal temperature of 30° C.

Figure 18:
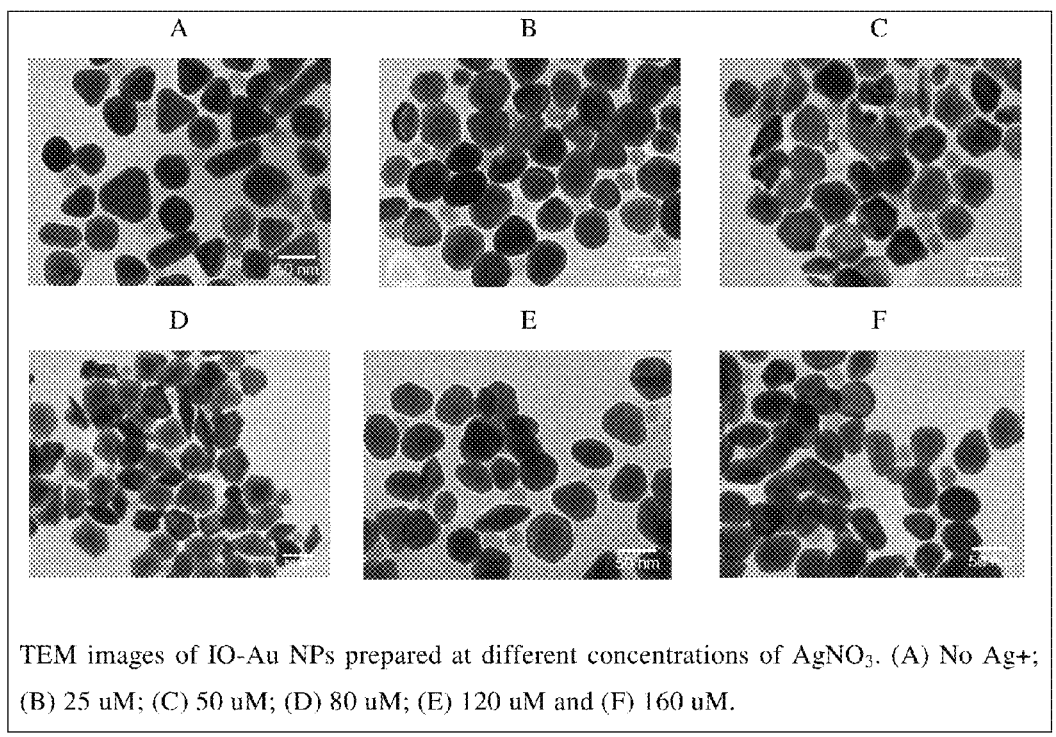
FIG. 18 shows TEM images of TO-Au NPs prepared at different concentrations of $AgNO_3$. (A) No Ag+; (B) 25 uM; (C) 50 uM; (D) 80 uM; (E) 120 uM and (F) 160 uM.

The mechanism of the preferential growth specifically into hexagon at 30° C. is not clear at this stage. A general model for the formation of various shapes of metal NPs is the outcome of the interplay between the faceting binding tendency of the stabilizing agents and the growth kinetics. The growth kinetics is dependent on both the concentration of AA and the temperature of the solution. Increasing AA concentration led to the transition of the morphology of core-shell NPs from oval to pin shapes at 22° C. Thus, temperature is the key factor in determining the formation of hexagonal NPs. Another important chemical in the growth solution is $AgNO_3$. $AgNO_3$ has been used to control the aspect ratio of gold nanorods (Nikoobakht, B., M. A. El-Sayed, Chem. Mater., 15(10): 1957-1961 (2013)). It has been proposed that $Ag^+$ is reduced to form $Ag^0$ on metal surface with a surface potential less than the standard reduction potential of $Ag^+$. The deposition of $Ag^0$ on the side {111} facet of gold nanorods is faster than on the end {100} facet due to lower reduction potential on the side facet. This inhibits the rod growth on the side facet leading to preferential growth of Au at the ends (Orendorff, C. J., et al., J. Phys. Chem. B, 110: 3990-3994 (2006)). To examine whether $Ag^+$ can tune the size of the NHGs, we prepared the NPs with various concentrations of AgNO$_3$ at 30° C. FIG. 18A shows TEM image of IO-Au NPs prepared without Ag+. NPs with several shapes were observed including spheres, triangles and rods. The surface of the spherical NPs shows faceted structure rather than smooth curvature. It is very interesting that when the NPs were grown in the presence of 25 uM Ag+, we did not find rod-shaped NPs (FIG. 18B). The triangle particle pollution was also decreased. The NPs were dominated with spherical ones with faceted surface. The faceted surface has some similarity to hexagonal geometry. When the concentration of Ag$^+$ was increased to 50 uM, the NPs was dominated with hexagonal NPs (~60% of all NPs) with some of them having irregular edges (FIG. 18C). It is very clear that Ag$^+$ is important in controlling the final shape of the NPs. It facilitated the anisotropic growth of the Au shell into the hexagonal shape. When the concentration of Ag+ was further increased to 120 uM, more hexagonal NPs with well defined structure were found (FIG. 18D). However, further increase of the concentration of Ag+ resulted in the formation of NPs in both hexagon and oval shapes (FIG. 18E). In fact, the oval NPs appear to grow from the hexagonal NPs, with fastest Au deposition on one of the six faces of the NPs. Continued increase of the concentration of Ag$^+$ ions further increased the population of oval NPs (FIG. 18F). These results indicate that the surface facets of the NPs may have different surface energy. Ag$^+$ is reduced to Ag$^0$ on these surfaces with different reduction potential and thus with different speed. Correspondingly, Au is deposited onto the facet that is not inhibited by Ag, leading to growth of the hexagonal NPs into oval shapes. These speculations needs to be tested with high resolution TEM studies and chemical analysis.

Figure 19:
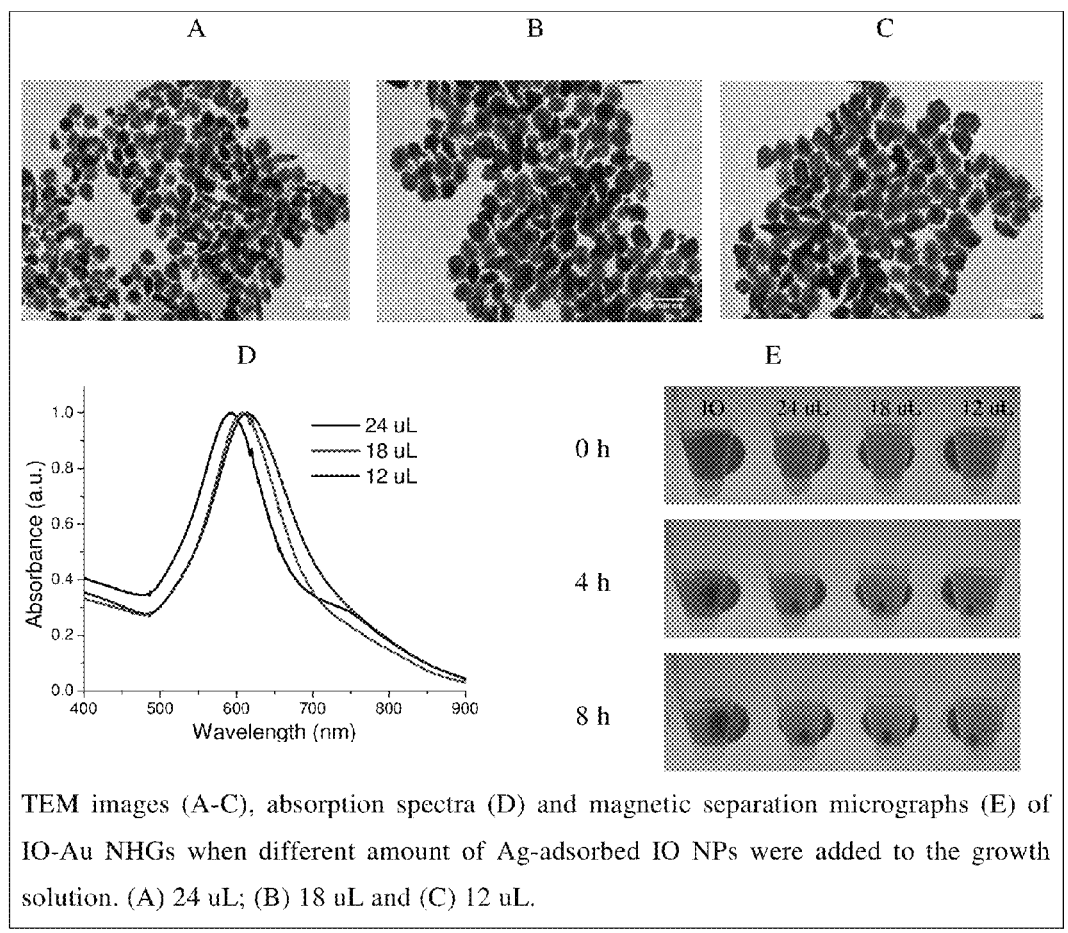
FIG. 19 shows TEM images (A-C), absorption spectra (D) and magnetic separation micrographs (E) of TO-Au NHGs when different amount of Ag-adsorbed TO NPs were added to the growth solution. (A) 24 uL; (B) 18 uL and (C) 12 uL.

By varying the amount of Ag-adsorbed IO seed NPs, we further made IO-Au NHGs with different shell thickness. FIG. 19A-C shows TEM images of IO-Au NHGs prepared by adding 24, 18 and 12 uL the seed NPs. The addition of 24, 18 and 12 uL seed NPs led to the formation of IO-Au NHGs with the average size in the diagonal length of 50, 60 and 70 nm, respectively. Considering the IO core of 25 nm and the thickness of PMAO of 4 nm, the thickness of Au shell in the diagonal direction was estimated to be about 8, 13 and 18 nm, respectively. The LSPR of the core-shell NPs red shifted when the thickness of the Au shell was increased (FIG. 19D). While the LSPR of the 50 nm NPs was 592 nm, the LSPR of 70 nm ones was 616 nm. Similar optical shifts were observed in previous studies on IO-Au core-shell nanospheres without polymer gap (Xu, Z., Y. Hou, S. Sun, J. Am. Chem. Soc., 129(28):8698-8699 (2007)).

The magnetic properties of the IO-Au NHGs were tested by their separation from solution using permanent magnets (FIG. 19E). The 25 nm PMAO-coated IO NPs were used for comparison. The Au-coated IO NPs showed similar separation rate to the IO NPs. At 4 h after attachment to a 12-tube magnet (surface field: ~5000 Gauss), most NPs were separated from the solution and attracted to the magnet. At 8 h, all NPs in the solution were attracted to the magnet. The Au coating increased the density of the IO NPs. Thus, the IO-Au NHGs were concentrated in the vial at a location lower than the bare IO NPs. The studies in turn confirmed the formation of IO-Au core-shell NPs rather than solid Au NPs.

Figure 20:
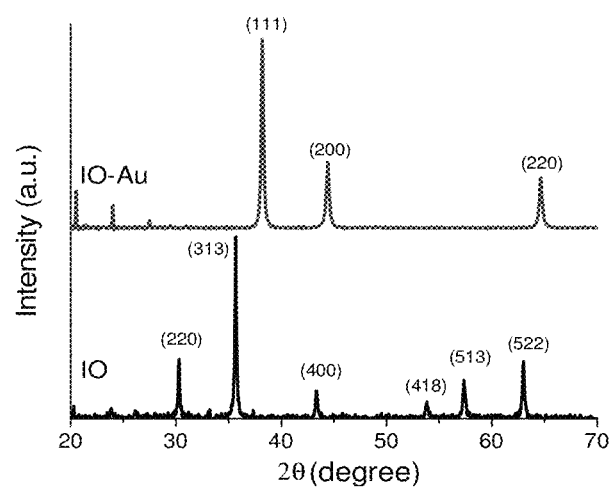
FIG. 20 shows the X-ray diffraction (XRD) patterns of the TO (bottom) and TO-Au (top) NHGs NPs (50 nm).

FIG. 20 shows the X-ray diffraction (XRD) patterns of the IO and IO-Au NHGs NPs (50 nm). The position and relative intensity of the diffraction peaks form IO NPs match well with those from standard spinel-structured Fe$_3$O$_4$ powder (Cornell, R. M., U. Schwertmann., ed. *The iron oxides: structure properties, reactions, occurrence and uses*. Pp. 167-168, VCH: New York (1996)). The gold-coated NPs exhibit the diffraction peaks for face-centered cubic (fcc) Au. No diffraction peaks from IO were observed in the core-shell structures. Previous studies showed that the diffraction from inner IO is too weak to be detected when the thickness of Au is and larger than 2.5 nm due to the heavy atom effect of Au. In our IO-Au NHGs, the thickness of Au is larger than 5 nm. Thus, it is not surprising that only the diffraction pattern from Au was detected.

Figure 21:
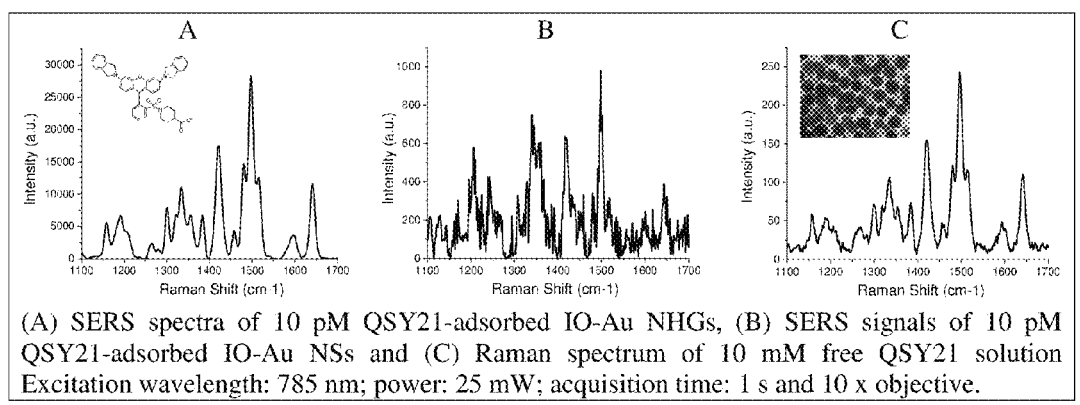
FIG. 21 shows SERS spectra of NPs. (A) SERS spectra of 10 pM QSY21-adsorbed TO-Au NHGs, (B) SERS signals of 10 pM QSY21-adsorbed TO-Au NSs and (C) Raman spectrum of 10 mM free QSY21 solution Excitation wavelength: 785 nm; power: 25 mW; acquisition time: 1 s and 10× objective.

A major feature of metal NPs is their ability to enhance Raman signals of adsorbed molecules. Due to the excitation of the LSPR, the SERS enhancement factors can be orders of magnitude depending on the size, shape and composition of the metal. This makes metal NPs attractive contrast agents for sensitive molecular detection. Here we examined the Raman enhancement capability of IO-Au NHGs using QSY21 Raman reporters. QSY21 is non-fluorescent organic dye molecules with delocalized electrons (FIG. 21 inset), well suited for SERS studies. QSY 21 was nonspecifically adsorbed onto IO-Au NHGs (60 nm in diagonal length) through electrostatic and electronic interactions. The dye-adsorbed particles were stabilized with thiolated PEG that covalently binds to the metal surface without displacing the dye molecule. To ensure saturated coating, excessive QSY 21 was added (QYS21: NHG=50,000:1) during preparation. By determining the free QSY21 in solution with high performance liquid chromatography, we estimated the surface density of QSY21 was 2.0×10$^4$ QSY 21 per particle. FIG. 21A shows the SERS spectra of 10 pM (NP concentration) QSY21-adsorbed IO-Au NHGs. The particles gave intense Raman signals within 1 s at low laser power (25 mW) under NIR excitation (785 nm). Based on the QSY21 surface density, the equivalent concentration of QSY21 was estimated to be 0.2 µM. The strong bands at 1333, 1584 and 1641 cm$^{-1}$ are from the characteristic xanthene ring stretching vibrations in QSY21. To determine the SERS enhancement factor (EF), we measured the Raman signals from free QSY21 solution under the same condition. The Raman spectrum from 10 mM QSY21 solution is shown in FIG. 21B. The signals are very weak and noisy. We selected the well-resolved peak at 1642 cm$^{-1}$ to calculate the EF value. Based on the signal intensities in FIG. 21A and FIG. 21B at 1642 cm$^{-1}$ and the concentrations of QSY21 in these two samples, we calculated the EF value for QSY21 by the IO-Au NHGs is 1.5×10$^6$. As a comparison, we measured the EF value for IO-Au NSs with similar dimension (~60 nm in diameter). The IO-Au NSs were prepared in the growth solution containing 0.53 mM AA and 10 µM AgNO$_3$ at 25° C. (FIG. 21C inset). The NSs were coated with QSY21 using the same procedure to the NHGs. FIG. 5C shows the SERS spectrum from 10 pM QSY21-adsorbed IO-Au NSs. The signals are much weaker than that from NHGs. The EF value is calculated to be 1.4×10$^4$. This is about 107 times lower than the NHGs. Such high SERS activities associated with the NHGs is not surprising. This is because the sharp cores on the hexagons create hot spots, leading to large E-field enhancement (Hao, E., Schatz, G., Hupp, J., J. Fluor., 14(4):331-34 (2004).

Figure 22:
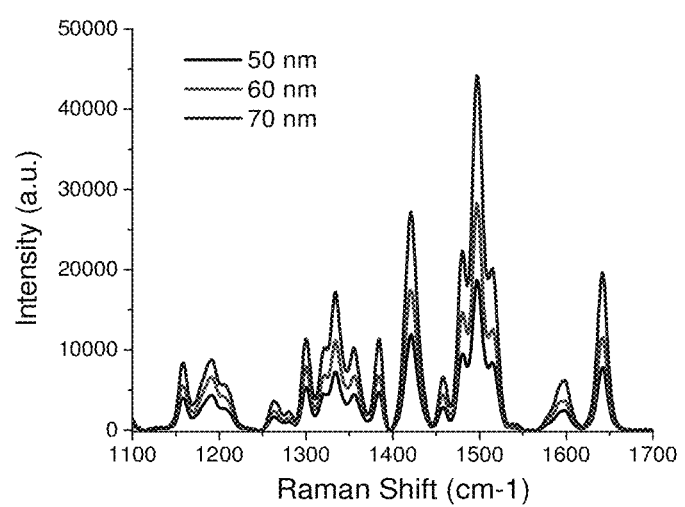
FIG. 22 shows SERS spectra from 10 pM QSY-adsorbed TO-Au NHGs of 50, 60 and 70 nm.

We further compared the SERS activities of the IO-Au NHGs with different sizes. FIG. 22 shows SERS spectra from 10 pM QSY-adsorbed IO-Au NHGs of 50, 60 and 70 nm. These three sized-NPs have the same core, but different shell thickness. The thickness in the diagonal direction for these NPs are 8, 13 and 18 nm, respectively. The SERS results showed that the signal intensity of QSY21 increased as the shell thickness increased. The ratio of signal intensity at 1642 cm$^{-1}$ band for the 50, 60 and 70 nm NHGs is 1:1.5:2:3. The surface density of QSY21 on these NPs was $1.1\times10^4$, $2\times10^4$, $2.7\times10^4$ QSY per particle, respectively. Thus, the difference of the signal intensity from these NPs are most likely due to the difference in the surface density of QSY21 on these NPs.

CONCLUSION

We have prepared IO-Au core-shell NPs in hexagonal shapes by adapting our previously developed seed-mediated growth method. The method uses Ag-adsorbed magnetite NPs as the seed NPs to induce anisotropic growth of the Au shell in a growth solution containing CTAB, $HAuCl_4$, $AgNO_3$ and AA. By controlling the temperature of the growth condition at 30° C. and the growth solution with 0.1 MCTAB, 0.4 mM $HAuCl_4$, 80 uM $AgNO_3$ and 0.67 mMAA, we have made IO-Au NHGs with high quality and purity. Systematic studies on the temperature effects showed that at temperature lower than 30° C., NPs in oval shapes dominated. At temperature higher than 30° C., the NPs turned out to be more spherical. We also found that $Ag^+$ is also important in directing the hexagonal geometry. Without $Ag^+$, the NPs were mainly spheres with impurities of triangle and rod-shaped NPs. Low concentration of $Ag^+$ increased the homogeneity of the NPs in spheres and induced a faceted structure on the surface of the spherical NPs. The concentration of $Ag^+$ higher than 80 uM induced transition of hexagonal NPs into ovals. Future studies with HRTEM and energy disperse X-ray spectroscopy (EDX) are needed to gain insights on growth mechanism. The IO-Au NHGs with different shell thickness were readily made by changing the amount of the Ag-adsorbed IO seed NPs, with less amount of seed NPs for NPs with thicker Au shell. Structural studies with XRD revealed a fcc crystal structure of the Au shell. The IO-Au NHGs exhibit good magnetic separation, similar to the IO core NPs. The NHGs exhibited 100 times better SERS activities than the spherical counterparts, with a SERS EF on the scale of $10^6$. Increasing the shell thickness of Au increased the SERS activities due to increased surface density of the adsorbed molecules for larger NPs. The IO-AU NHGs will provide a new platform for a wide range of applications from biological separation to ultrasensitive molecular detection.

REFERENCES

1. M. Mikhaylova, M., D. K. Kim, N. Bobrysheva, M. Osmolowsky, V. Semenov, T. Tsakalakos, M. Muhammed., Superparamagnetism of magnetite nanoparticles: dependence on surface modification. Langmuir, 2004, 20: p., 2472-2477.
2. J. L. Lyon, J. L., D. A. Fleming, M. B. Stone, P. Schiffer, M. E. Williams, Synthesis of Fe Oxide Core/Au shell nanoparticles by iterative hydroxylamine seeding. Nano Lett., 2004. 4(4): p., 719-723.
3. L. Wang, L., J. Luo, M. M. Maye, Q. Fan, Q. Rendeng, M. H. Engelhard, C. Wang, Y. Lin, C. J. Zhong, Iron oxide-gold core-shell nanoparticles and thin film assembly. J. Mater. Chem., 2005. 15: p., 1821-1832.
4. Q. H. Lu, Q. H., K. L. Yao, D. Xi, Z. L. Liu, X. P. Luo, Q. Ning, Synthesis and characterization of composite nanoparticles comprised of gold shell and magnetic core/cores. J. Magn. Magn. Mater., 2006, 301: p., 44-49.
5. Z. Xu, Z., Y. Hou, S. Sun, Magnetic Core/Shell $Fe_3O_4$/Au and $Fe_3O_4$/Au/Ag nanoparticles with tunable plasmonic properties. J. Am. Chem. Soc., 2007, 129(28): p., 8698-8699.
6. T. T. H. Pham, T. T. H., C. Cao, S. J. Sim, Application of citrate-stabilized gold-coated ferric oxide composite nanoparticles for biological separations. J. Magn. Magn. Mater., 2008. 320: p., 2049-2055.
7. M. Mandal, M., S. Kundu, S. K. Ghosh, S. Panigrahi, T. K. Sau, S. M. Yusuf, T. Pal, Magnetite nanoparticles with tunable gold or silver shell. J. Colloid. Interf. Sci., 2005, 286: p. 187-194.
8. U. Tamer, U., Y. Gundogdu, I. H. Boyacl, K. Pekmez, Synthesis of magnetic core-shell $Fe_3O_4$—Au nanoparticle for biomolecule immobilization and detection. J Nanopart Res, 2010, 12: p., 1187-1196.
9. J. Lim, J., A. Eggeman, F. Lanni, R. D. Tilton, S. M. Majetich. Synthesis and single-particle optical detection of low-polydispersity plasmonic-superparamagnetic nanoparticles. Adv. Mater., 2008, 20: p., 1721-1726.
10. S. F. Chin, S. F., K. S. Iyer, C. L. Raston, Facile and green approach to fabricate gold and silver coated superparamagnetic nanoparticles. Cryst. Growth Des., 2009, 9: p., 2685-2689.
11. Y. Jin, C. Y., Jia, C., S. W. Huang, S. W., M. O'Donnel, M., X. Gao, X., Multifuncional nanoparticles as coupled contrast agents. Nat. Commun., 2010, 1(41):, p. 1-8.
12. X. Ji, R. Shao, A. M. Elliott, R. J. Stafford, E. Esparza-Coss, G. Liang, Z. P. Luo, K. Park, J. T. Markert, C. Li. Ji, X. e. a., Bifunctional gold nanoshells with a superparamagnetic iron oxide-silica core suitable for both MR imaging and photothermal therapy. J. Phys. Chem. C, 2007, 2007: p. 111, 6245-6251.
13. L. Wang, L., J. Bai, Y. Li, Y. Huang, Multifunctional nanoparticles displaying magnetization and near-IR absorption. Angew. Chem. Int. Ed., 2008, 47: p., 2439-2442.
14. Q. Zhang, Q., J. Ge, J. Goebl, Y. Hu, Y. Sun, Y. Yin, Tailored synthesis of superparamagnetic gold nanoshells with tunable optical properties. Adv. Mater., 2010. 22: p., 1905-1909.
15. H. Y. Park, H. Y., M. J. Schadt, L. Wang, I. I. S. Lim, P. N. Njoki, S. H. Kim, M. Y. Jang, J. Luo, C. J. Zhong, Fabrication of magnetic Core-Shell Fe oxide-Au nanoparticles for interfacial bioactivity and bio-separation. Langmuir, 2007, 23: p. 9050-9056.
16. E. Hao, E., Schatz, G., Hupp, J., Synthesis and optical properties of anisotropic metal nanoparticles. J. Fluor., 2004, 14(4),: p. 331-341.
17. R. Weissleder, R., A clearer vision for in vivo imaging. Nat. Biotechnol., 2001, 19: p., 316-317.
18. Q. Wei, Q., H. M. Song, A. P. Leonov, J. A. Hale, D. Oh, Q. K. Ong, K. Ritchie, A. Wei, Gyromagnetic imaging: dynamic optical contrast using gold nanostars with magnetic cores. J. Am. Chem. Soc., 2009, 131: p. 9728-9734.
19. H. M. Song, H. M., Q. Wei, Q. K. Ong, A. Wei, Plasmon-resonant nanoparticles and nanostars with magnetic cores: synthesis and magnetomotive imaging. ACS Nano, 2010, 4: p., 5163-5173.
20. T. R. Geiger, T. R., D. S. Peeper, Metastasis mechanisms. Biochimica et Biophysica Acta 2009, 1796: p., 293-308.
21. P. Paterlini-Brechot, P., Benali, N. L., Circulating tumor cells (CTC) detection: Clinical impact and future directions. Cancer Lett., 2007, 253: p. 180-204.
22. K. Jacob, K., C. Sollier, N. Jabado, Circulating tumor cells: detection, molecular profiling and future prospects. Expert Rev Proteomics, 2007, 4(6):, p. 741-756.
23. B. Mostert, B., S. Sleijfer, J. A. Foekens, J. W. Gratama, Circulating tumor cells (CTCs): Detection methods and their clinical relevance in breast cancer. Cancer Treat. Rev., 2009, 35: p. 463-467.

24. M. Alunni-Fabbroni, M., M. T. Sandri., Circulating tumour cells in clinical practice: Methods of detection and possible characterization. Methods, 2010, 50(4): p., 289-297.
25. M. Yu, M., S. Stott, M. Toner, S. Maheswaran, D. A. Haber, Circulating tumor cells: approaches to isolation and characterization. J. Cell Biol., 2011, 192: p., 373-382.
26. S. Riethdorf, S., H. Fritsche, V. Muller, T. Rau, C. Schindibeck, B. Rack, W. Janni, C. Coith, K. Beck, F. Janicke, S. Jackson, T. Gornet, M. Cristofanilli, K. Pantel, Detection of circulating tumor cells in peripheral blood of patients with metastatic breast cancer: A validation study of the CellSearch system. Clin Cancer Res., 2007, 13(3): p. 920-928.
27. W. E. Doering, W. E., M. E. Piotti, M. J. Natan, R. G. Freeman, SERS as a foundation for nanoscale, optically detected biological labels. Adv. Mater., 2007, 19: p., 3100-3108.
28. S. Nie, S. R. S., Emory, S. R., Probing single molecules and single nanoparticles by surface-enhanced Raman scattering. Science, 1997, 275(5303): p., 1102-1106.
29. M. Y. Sha, H. X. M. Y., Xu, H. X., M. J. Natan, M. J., R. Cromer, R., Surface-enhanced Raman S scattering tags for rapid and homogeneous detection of circulating tumor cells in the presence of human whole blood. J. Am. Chem. Soc., 2008, 130(51): p., 17214-17215.
30. X. Wang, X., X. M. Qian, X. M., J. J. Beitler, J. J., Z. G. Chen, Z. G., F. R. Khuri, F. R., M. M. Lewis, M. M., H. J. C. Shin, H. J. C., S. M. Nie, S M., D. M. Shin, D. M., Detection of circulating tumor cells in human peripheral blood using surface-enhanced Raman scattering nanoparticles. Cancer Research, 2011, 71, (5): p. 1526-1532.
31. E. V. Shtykova., E. V., Hydrophilic monodisperse magnetic nanoparticles protected by an amphiphilic alternating copolymer. J. Phys. Chem. C, 2008, 112: p., 16809-16817.
32. E. I. Galanzha, E. I., E. V. Shashkov, E. V., T. Kelly, T., J. W. Kim, J. W., L. Yang, L, V. P. Zharov, V. P., In vivo magnetic enrichment and multiplex photoacoustic detection of circulating tumour cells. Nat. Nanotechnol., 2009, 4: p., 855-860.
33. H. Xu, H., Z. P. Aguilar, L. Yang, M. Kuang, H. Duan, Y. Xiong, H. Wei, A. Wang, Antibody conjugated magnetic iron oxide nanoparticles for cancer cell separation in fresh whole blood. Biomater., 2011, 32, pp. 9758-9765.

The contents of each of the patents, patent applications, and references cited herein are incorporated herein by reference in their entireties.

Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the invention.

What is claimed is:

1. A method of detecting a circulating tumor cell (CTC) in a sample, the method comprising:
    contacting the sample with a Raman reporter coated iron oxide-gold core-shell nanoparticle conjugated to a specific binding pair capable of specifically binding with the CTC; and
    detecting the presence of the Raman reporter coated iron oxide-gold core-shell nanoparticle bound to the CTC by surface-enhanced Raman spectroscopy (SERS), thereby detecting the CTC, wherein the Raman reporter coated iron oxide-gold core-shell nanoparticle comprises a gold shell onto a silver adsorbed iron-oxide nanoparticle core and said Raman reporter is coated onto the gold shell, and wherein said Raman reporter comprises organic dye with delocalized electrons,
    wherein the sample comprises whole blood,
    wherein the Raman reporter coated iron oxide-gold core-shell nanoparticle is anisotropic such that the Raman reporter coated iron oxide-gold core-shell nanoparticle is magnetic-optical hybrid, and the circulating tumor cell is detected and captured by the Raman reporter coated iron oxide-gold core-shell nanoparticle conjugated to the specific binding partner capable of specifically binding with the CTC, and
    wherein a limit of detection (LOD) of the CTC is less than 2 cells/ml whole blood.

2. The method of claim 1, wherein the Raman reporter coated iron oxide-gold core-shell nanoparticle is nanooval.

3. The method of claim 1, wherein the specific binding pair is an antibody capable of specifically binding the CTC.

4. The method of claim 1, wherein the method includes the step of magnetically separating the Raman reporter coated iron oxide-gold core-shell nanoparticle bound to the CTC from the sample.

5. The method of claim 1, wherein the step of detecting comprises detecting the presence of the Raman reporter coated iron oxide-gold core-shell nanoparticle in an integrated flow system, thereby capturing and detecting the CTC.

6. The method of claim 1, wherein the limit of detection (LOD) is less than 1 cell/ml whole blood.

7. A method of isolating a circulating tumor cell (CTC) from a blood sample, the method comprising:
    mixing the blood sample with a Raman reporter coated iron oxide-gold core-shell nanoparticle conjugated to a specific binding pair capable of specifically binding with the CTC present in the sample, to provide a mixed sample, loading the mixed sample into a capillary;
    separating the CTC bound to the Raman reporter coated iron oxide-gold core-shell nanoparticle; and
    detecting the presence of the Raman reporter coated iron oxide-gold core-shell nanoparticle bound to the CTC by surface-enhanced Raman spectroscopy (SERS), wherein the Raman reporter coated iron oxide-gold core-shell nanoparticle comprises a gold shell onto a silver adsorbed iron-oxide nanoparticle core and said Raman reporter is coated onto the gold shell, and wherein said Raman reporter comprises organic dye with delocalized electrons;
    wherein the Raman reporter coated iron oxide-gold core-shell nanoparticle is anisotropic such that the iron oxide-gold core-shell nanoparticle is magnetic-optical hybrid, and the circulating tumor cell in the blood is captured by the iron oxide-gold core-shell nanoparticle conjugated to the specific binding partner capable of specifically binding with the CTC, and
    wherein a limit of detection (LOD) of the CTC is less than 2 cells/ml whole blood.

8. The method of claim 7, wherein the CTC is separated in a flow system or in a microfluidic device comprising externally attached magnet.

9. The method of claim 7, wherein the CTC is separated from a region of the capillary where the present of the Raman reporter coated iron oxide-gold core-shell nanoparticle bound to the CTC is detected.

10. The method of claim 1, wherein the Raman reporter coated iron oxide-gold core-shell nanoparticle is detected by a portable Raman spectrometer.

11. The method of claim 10, wherein the Raman reporter is QSY21.

12. The method of claim 7, wherein the Raman reporter coated iron oxide-gold core-shell nanoparticle is detected by a portable Raman spectrometer.

13. The method of claim 12, wherein the Raman reporter is QSY21.

14. A method of isolating and detecting a circulating tumor cell (CTC) in a sample, the method comprising:
   contacting the sample with a Raman reporter coated iron oxide-gold core-shell nanoparticle conjugated to a specific binding pair capable of specifically binding with the CTC, wherein the Raman reporter coated iron oxide-gold core-shell nanoparticle comprises a gold shell onto a silver adsorbed iron-oxide nanoparticle core and said Raman reporter is coated onto the gold shell, and wherein said Raman reporter comprises organic dye with delocalized electrons;
   isolating the CTC bound with the Raman reporter coated iron oxide-gold core-shell nanoparticles in a flow system or in a microfluidic device comprising an externally attached permanent magnet,
   detecting the isolated CTCs bound with the Raman reporter coated iron oxide-gold core-shell nanoparticles by a Raman spectrometer in the flow system or a Raman microscope in the microfluidic device based on surface-enhanced Raman spectroscopy (SERS),
   wherein the sample comprises whole blood,
   wherein the Raman reporter coated iron oxide-gold core-shell nanoparticle is anisotropic such that CTC attached with the Raman reporter coated iron oxide-gold core-shell nanoparticle particle can be dually isolated with magnetic isolation and detected with SERS based of the magnetic-optical core-shell structure and the anisotropic property,
   wherein a limit of detection (LOD) of the CTC is less than 2 cells/ml whole blood.

15. The method of claim 14, further comprising:
   profiling surface protein expressions on CTCs at single cell resolution by the Raman microscope.

* * * * *